(12) United States Patent
Marck

(10) Patent No.: US 6,833,421 B1
(45) Date of Patent: Dec. 21, 2004

(54) COMPOUND

(75) Inventor: Guy Marck, Schlierbach (FR)

(73) Assignee: Rolic AG, Zug (CH)

( * ) Notice: Subject to any disclaimer, the term of this patent is extended or adjusted under 35 U.S.C. 154(b) by 0 days.

(21) Appl. No.: 10/030,481

(22) PCT Filed: Jul. 17, 2000

(86) PCT No.: PCT/EP00/06788

§ 371 (c)(1),
(2), (4) Date: Jan. 9, 2002

(87) PCT Pub. No.: WO01/07495

PCT Pub. Date: Feb. 1, 2001

(30) Foreign Application Priority Data

Jul. 23, 1999 (EP) ............................................ 99305857

(51) Int. Cl.$^7$ ............................................ C08F 220/68

(52) U.S. Cl. .................... 526/326; 526/292.1; 526/293; 526/297; 526/279; 526/304; 526/305; 526/311; 526/328; 526/347; 526/321; 349/167

(58) Field of Search ................................. 526/326, 293, 526/292.1, 297, 279, 304, 305, 311, 328, 321, 347, 245, 248; 349/167, 124, 177

(56) References Cited

U.S. PATENT DOCUMENTS

| 5,326,495 | A | | 7/1994 | Eidenschink |
| 5,539,074 | A | | 7/1996 | Herr et al. |
| 5,602,661 | A | | 2/1997 | Schadt et al. |
| 5,681,504 | A | * | 10/1997 | Buchecker et al. ..... 252/299.61 |
| 5,800,733 | A | | 9/1998 | Kelly |
| 5,800,734 | A | * | 9/1998 | Buchecker et al. ..... 252/299.61 |
| 5,965,761 | A | * | 10/1999 | Buchecker et al. ......... 556/440 |
| RE36,625 | E | | 3/2000 | Herr et al. |
| 6,107,427 | A | | 8/2000 | Herr et al. |

FOREIGN PATENT DOCUMENTS

| EP | 0 611 786 | 8/1994 |
| EP | 0 755 918 | 1/1997 |
| EP | 0 763 552 | 3/1997 |
| WO | WO 91/16295 | 10/2001 |

* cited by examiner

Primary Examiner—Tatyana Zalukaeva
(74) Attorney, Agent, or Firm—Finnegan, Henderson, Farabow, Garrett & Dunner, L.L.P.

(57) ABSTRACT

New photoactive polymers, their use as liquid crystal (LC) orientation layers and their use in the construction of unstructured and structured optical and electro-optical elements and multi-layer systems. The new photoactive polymers are crosslinkable polymers that can be readily cross linked over a relatively short irradiation time.

11 Claims, No Drawings

COMPOUND

This application is a national stage filing under 35 U.S.C. § 371 of international application no. PCT/EP00/06788, filed on Jul. 17, 2000, which published in the English language. This application also claims the benefit of priority under 35 U.S.C. § 119(a) to European patent application no. 99305857.7, filed on Jul. 23, 1999.

The present invention relates to new photoactive polymers, their use as liquid crystal (LC) orientation layers and their use in the construction of unstructured and structured optical and electro-optical elements and multi-layer systems.

The successful functioning of a Liquid Crystal Device relies upon the ability of the IC molecules within that device to assume and maintain an alignment imposed upon them. Alignment of the LC molecules is achieved by use of an orientation layer which defines a direction of orientation for the LC molecules of the device with the result that the longitudinal axes of the molecules become aligned with the direction of orientation defined by the orientation layer. In addition to this directional alignment, the orientation layer is also able to impart to the LC molecules an angle of tilt so that the molecules align themselves at an angle to the surface of the orientation layer rather than lying parallel thereto.

Tilt angles of between 1° and 15° are usual for Nematic LCDs. Tilt angles of about 7° are required for supertwisted nematic (STN) LCDs in order to avoid the formation of so-called fingerprint textures. Vertically aligned nematic (VAN) LCD's for instance require pretilt angles of between 85° and 90°.

Methods of preparing structured and unstructured orientation layers are well known to a skilled person. In particular it is known that by using linearly polarised light it is possible to prepare orientation layers in which both the direction of orientation and the tilt angle of the orientation layer are determined by the direction and angle of incidence of the plane polarised light used to irradiate said layer.

Structured orientation layers are of great interest in many areas of display technology and integrated optics. These layers are characterised by regions (pixels) which alternate in respect of the direction of orientation and angle of tilt of their component molecules. These orientation layers can be used to improve the viewing angle dependency of TN, STN and VAN LCDs, for example:

A possible method of producing high-resolution structured orientation patterns in liquid crystalline layers is described in *Jpn. J. Appl. Phys.*, Vol. 31 (1992), 2155. In that process the dimerisation of polymer-bonded photoreactive cinnamic acid groups induced by irradiation with linearly polarised light is employed for the structured orientation of liquid crystals. Those photo-oriented polymer networks can be used wherever structured or unstructured liquid crystal orientation layers are required. In addition to their use in LCDs, these orientation layers can also be used, for example, in the production of so-called hybrid layers, as illustrated in European Patent Applications EP-A-0 611 981, EP-A-0 689 084 and EP-A-0 689 065. It is possible, using these hybrid layers of photostructured orientation polymers and crosslinkable low molecular weight liquid crystals to prepare optical elements such as, non-absorptive colour filters, linear and circular polarisers, optical delay layers and so on.

The ability of the resulting orientation layers to perform their function thus depends, in part, upon the number of molecules in the layer that have been dimerised as a result of irradiation with linearly polarised light. The extent to which the molecules are dimerised relies, in part, on the irradiation time, the irradiation energy and the structure of the molecules being irradiated.

EP-A-0 611 786, EP-A-0 763 552, EP-A-0 860 455, WO 96/10049 and WO 99/15576 describe polymers that are suitable in principle for the production of such anisotropically crosslinked, photostructured orientation layers for liquid crystals.

However, a problem with many polymers currently used in the preparation of photo-orientated orientation layers is that relatively long irradiation times are required to effect efficient dimerisation of the component molecules. There is, therefore, a need for photo crosslinkable polymers that can be readily cross-linked over a relatively short irradiation time. The present invention addresses that need.

A first aspect of the present invention provides a polymeric compound comprising a repeating unit of formula (I)

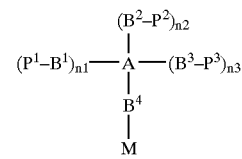

in which:

A represents a nitrogen atom, a carbon atom, a group —CR¹— or an aromatic or alicyclic group, which is optionally substituted by a group selected from fluorine, chlorine, cyano and a $C_{1-18}$ cyclic, straight-chain or branched alkyl group, which is optionally substituted by a single cyano group or by one or more halogen atoms and in which one or more non-adjacent alkyl —CH$_2$— groups are optionally replaced by a group selected from —O—, —CO—, —CO—O—, —O—CO—, —Si(CH$_3$)$_2$—O—Si(CH$_3$)$_2$—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C— and —O—CO—O—, wherein R$^1$ represents a hydrogen atom or lower alkyl, M represents a repeating monomer unit;

$n^1$ to $n^3$ each independently represent 0 or an integer having a value of from 1 to 3, with the proviso that $1 < n^1 + n^2 + n^3 < 4$;

$P^1$, $P^2$, $P^3$ each independently represents a photoactive group; and $B^1$ to $B^4$ each independently represent a residue of general formula II

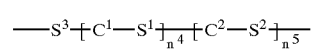

in which $S^1$ to $S^3$ each independently represent a single bond or a spacer group selected from a $C_{1-24}$ straight-chain or branched alkylene group, which is optionally substituted by a single cyano group or by one or more halogen atoms and in which one or more non-adjacent alkylene —CH$_2$— groups are optionally replaced by a group selected from —O—, —CO—, —CO—O—, —O—CO—, —Si(CH$_3$)$_2$—O—Si(CH$_3$)$_2$—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C— and —O—CO—O— wherein R$^1$ is as defined above, C¹ and C² each independently represents an aromatic or an alicyclic group, which is optionally substituted by a group selected from fluorine, chlorine, cyano or a $C_{1-18}$ cyclic, straight-chain or branched alkyl group, which is optionally substituted by a single cyano group or by one or more halogen atoms and in which one or more non-adjacent alkyl —$CH_2$— groups are optionally replaced by a group selected from —CO—, —CO—, —CO—O—, —O—CO—, —Si($CH_3$)$_2$—O—Si($CH_3$)$_2$—, —NR¹—, —NR¹—CO—, —CO—NR¹—, —NR¹—CO—O—, —O—CO—NR¹—, —NR¹—CO—NR¹—, —CH=CH—, —C≡C— and —O—CO—O— wherein R¹ represents a hydrogen atom or lower alkyl, and n⁴ and n⁵ are each independently 0 or 1.

The polymeric compounds of the present invention can be readily aligned upon exposure to linearly polarised light. In addition, by using the compounds of the invention, it is possible to reduce the irradiation time required to form cross-linked polymer films.

By the term "aromatic" it should be understood to include optionally substituted carbocylic and heterocyclic groups.

By the term "cyclic, straight-chain or branched alkyl group, which is optionally substituted by a single cyano group or by one or more halogen atoms and in which one or more non-adjacent —$CH_2$— groups are optionally replaced by a group selected from —O—, —CO—, —CO—O—, —O—CO—, —CH=CH— and —C≡C—," it should be understood to include groups selected from the group comprising methyl, ethyl propyl, isopropyl, butyl, isobutyl, sec-butyl tert-butyl pentyl, isopentyl, cyclopentyl, hexyl, cyclohexyl, heptyl, octyl, nonyl, decyl, undecyl, dodecyl 3-methylpentyl, allyl, but-3-en-1-yl, pent-4-en-1-yl, hex-5-en-1-yl, propynyl, butynyl, pentynyl, methoxy, ethoxy, propoxy, isopropoxy, butoxy, isobutoxy, sec-butoxy, tert-butoxy, pentyloxy, isopentyloxy, cyclopentyloxy, hexyloxy, cyclohexyloxy, heptyloxy, octyloxy, nonyloxy, decyloxy, undecyloxy, dodecyloxy, 3-methylpentyloxy, allyloxy, but-3-enyloxy, pent-4-enyloxy, cylohexylmethoxy, cyclopentylmethoxy, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, cyclopentyloxycarbonyl, hexyloxycarbonyl, cyclohexyloxy, carbonyl, octyloxycarbonyl, nonyloxycarbonyl, decyloxycarbonyl, undecyloxycarbonyl, dodecyloxycarbonyl, 3-methylpentyloxycarbonyl, allyloxycarbonyl, but-3-enyloxycarbonyl, pent-4-enyloxycarbonyl, cylohexylmethoxycarbonyl, cyclopentylmethoxycarbonyl, acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, pentylcarbonyloxy, isopentylcarbonyloxy, cyclopentylcarbonyloxy, hexylcarbonyloxy, cyclohexylcarbonyloxy, octylcarbonyloxy, nonylcarbonyloxy, decylcarbonyloxy, undecylcarbonyloxy, dodecylcarbonyloxy, 3-methylpentylcarbonyloxy, but-3-enyloxy, pent-4-enyloxy, acetyl, ethylcarbonyl, propylcarbonyl, isopropylcarbonyl, butylcarbonyl, isobutylcarbonyl, sec-butyl-carbonyl, pentylcarbonyl, isopentylcarbonyl, cyclohexylcarbonyl, octylcarbonyl, nonylcarbonyl, decylcarbonyl, undecylcarbonyl, dodecylcarbonyl, methoxyacetoxy, 1-methoxy-2-propoxy, 3-methoxy-1-propoxy, 2-methoxyethoxy, 2-isopropoxyethoxy, 1-ethoxy-3-pentyloxy, 3-butynyloxy, 4-pentynyloxy, 5-chloropentynyl, 4-pentynecarbonyloxy, 6-propyloxyhexyl, 6-propyloxyhexyloxy, 2-fluoroethyl, trifuoromethyl, 2,2,2-trifuoroethyl, 1H,1H-pentadecafluorooctyl, 1H,1H,7H-dodecafluoroheptyl, 2-(perfluorooctyl)ethyl, 2-(perfluorobutyl)ethyl, 2-(perfluorohexyl)ethyl, 2-(perfluorodecyl)ethyl, perfluoropropyl, perfluorobutyl, perfluoroheptyl, perluorooctyl, perfluorononyl, 1-fluoropropoxy, 1-fluoropentyloxy, 2-fluoropropoxy, 2,2-difluoropropoxy, 3-fluoropropoxy, 3,3-difluoropropoxy, 3,3,3-trifluoropropoxy, trifluoromethoxy and the like.

By the term "lower alkyl" it should be understood to include straight chain and branched hydrocarbon radicals having from 1 to 6 carbon atoms, preferably from 1 to 3 carbon atoms. Methyl, ethyl propyl and isopropyl groups are especially preferred.

By the term "alicyclic" it should be understood to include non-aromatic carbocyclic or heterocyclic ring systems with 3 to 20 carbon atoms.

The group A is preferably an optionally substituted aromatic group. It is also preferred that when the group A is optionally substituted by an alkyl group, one or more of the alkyl —$CH_2$— groups are optionally replaced by a group selected from —O—, —CO—, —CO—O—, —O—CO— and —CH=CH—.

It is especially preferred that A is selected from the group selected from 1,2,5-benzenetriyl, 1,3,5-benzenetriyl and 1,3,4,5-benzenetetrayl, which are optionally substituted by one or more fluorine atoms. The group B⁴ preferably occupies position 1 of the especially preferred group A.

It is preferred that when $n^1+n^2=2$ and $n^3=0$, A represents —CR¹— or an optionally substituted aromatic or alicyclic group. Alternatively, when $n^1=3$ and $n^2+n^3=0$, A represents an optionally substituted aromatic or alicyclic group only.

The groups P¹, P² and P³ can be photoisomensed or photodimerised on exposure to UV or laser light. The groups P¹ to P³ preferably undergo photocyclisation reactions. The groups P¹ to P³ are preferably represented by the general formulae IIIa and IIIb:

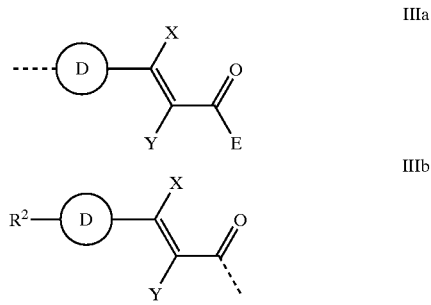

wherein the broken line indicates the point of linkage to S³ and wherein:

D represents pyrimidine-2,5-diyl, pyridine-2,5-diyl, 2,5-thiophenylene, 2,5-furanylene, 1,4- or 2,6-naphthylene; a phenylene group, which is optionally substituted by a group selected from fluorine, chlorine cyano; or a $C_{1-18}$ cyclic, straight-chain or branched alkyl residue, which is optionally substituted by a single cyano group or by one or more halogen groups and in which one or more non-adjacent alkyl —$CH_2$— groups are optionally replaced by a group selected from —O—, —CO—, —CO—O—, —O—CO—, —Si($CH_3$)$_2$—O—Si($CH_3$)$_2$—, —NR¹—, —NR¹—CO—, —CO—NR¹—, —NR¹—CO—O—, —O—CO—NR¹—, —NR¹—CO—NR¹—, —CH=CH—, —C≡C— and —O—CO—O—, wherein R¹ is as defined above;

E represents —OR$^3$, —NR$^4$R$^5$ or an oxygen atom, which defines together with the ring D a coumarin unit, wherein R$^3$, R$^4$ and R$^5$ are selected from hydrogen and a C$_{1-18}$ cyclic, straight-chain or branched alkyl residue, which is optionally substituted by one or more halogen atoms and in which one or more non-adjacent alkyl —CH$_2$— groups are optionally replaced by a group selected from —CO—, —CO—, —CO—O—, —O—CO— and —CH=CH—, or R$^4$ and R$^5$ together form a C$_{5-8}$ alicyclic ring;

X, Y each independently represent hydrogen, fluorine, chlorine, cyano or a C$_{1-12}$ alkyl group, which is optionally substituted by fluorine and in which one or more non-adjacent alkyl —CH$_2$— groups are optionally replaced by a group selected from —O—, —CO—O—, —O—CO— and —CH=CH—;

R$^2$ represents hydrogen or a C$_{1-18}$ straight-chain or branched alkyl residue, which is optionally substituted by a single cyano group or by one or more halogen atoms and in which one or more non-adjacent alkyl —CH$_2$— groups are independently optionally replaced by a group selected from —O—, —CO—, —CO—O—, —O—CO—, —Si(CH$_3$)$_2$—O—Si(CH$_3$)$_2$—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C— and —O—CO—O—, wherein R$^1$ is as defined above.

It is preferred that the groups X and Y represent hydrogen.

It is also preferred that the group D is selected from pyrimidine-2,5-diyl, pyridine-2,5-diyl, 2,5-thiophenylene, 2,5-furanylene, 1,4- or 2,6-naphthylene and a phenylene group, which is optionally substituted by a C$_{1-12}$ cyclic, straight-chain or branched alkyl residue, which alkyl group is optionally substituted by one or more halogen groups and in which one or more non-adjacent alkyl —CH$_2$— groups are independently optionally replaced by a group selected from —O—, —CO—, —CO—O—, —O—CO—, —CH=CH— and —C≡C—.

It is especially preferred that D is selected from pyrimidine-2,5-diyl, pyridine-2,5-diyl, 2,5-furanylene, 1,4- or 2,6-naphthylene and phenylene, which is optionally substituted by a C$_{1-6}$ straight-chain or branched alkyl residue, which alkyl group is optionally substituted by one or more fluorine atoms, and wherein one or more non-adjacent alkyl —CH$_2$— groups are independently optionally replaced by a group selected from —O—, —CO—, —CO—O—, —O—CO— and —CH=CH—.

By the term "phenylene" it should be understood to include 1,2-, 1,3- or 1,4-phenylene, which is optionally substitutes. It is preferred that the phenylene group is either a 1,3- or a 1,4-phenylene, 1,4-phenylene groups are especially preferred.

Preferred groups E are selected from —OR$^3$ and —NR$^4$R$^5$, wherein R$^3$ and R$^4$ represent a C$_{1-18}$ cyclic, straight-chain or branched alkyl residue, which is optionally substituted by one or more halogen atoms, and in which one or more non-adjacent alkyl —CH$_2$— groups are independently optionally replaced by —O— or —CH=CH—, wherein R$^5$ is selected from a hydrogen atom or a C$_{1-18}$ cyclic, straight-chain or branched alkyl residue, which is optionally substituted by one or more halogen groups and which one or more non-adjacent alkyl —CH$_2$— groups are optionally independently replaced by —O— or —CH=CH—, or R$^4$ and R$^5$ together to form a C$_{5-8}$ alicyclic ring.

It is especially preferred that E is selected from the group comprising —OR$^3$ or —NHR$^4$, wherein R$^3$ and R$^4$ represent a C$_{1-18}$ cyclic, straight-chain or branched alkyl residue which is optionally substituted by one or more fluorine atoms and in which one or more non-adjacent alkyl —CH$_2$— groups are independently optionally replaced —O—.

Preferred groups B1 to B4 are groups of formula II where n$^4$+n$^5$≤1.

It is preferred that each of the groups C$^1$ and C$^2$ comprising the groups B$^1$ to B$^4$ are selected from cyclohexane-1,4-diyl, pyrimidine-2,5-diyl, pyrdine-2,5-diyl, 1,4- or 2,6-naphthylene and phenylene, which is optionally substituted by one or more groups selected from fluorine, chlorine, cyano and a C$_{1-12}$ cyclic, straight-chain or branched alkyl residue, which is optionally substituted by a single cyano group or by one or more halogen atoms and in which one or more non-adjacent allyl —CH$_2$— groups are optionally independently replaced by a group selected from —O—, —CO—, —CO—O—, —O—CO—, —CH=CH—, —C≡C— and —O—CO—O—.

It is especially preferred that the groups C$^1$ and C$^2$ are selected from cyclohexane-1,4-diyl, pyrimidine-2,5-diyl, pyridine-2,5-diyl, 2,6-naphthylene and phenylene, which is optionally substituted by one or more fluorine atoms or a C$_{1-8}$ straight-chain or branched alkyl residue, which is optionally substituted by one or more fluorine atoms, and in which one or more non-adjacent alkyl —CH$_2$— groups arm independently optionally replaced by a group selected from —O—, —CO—, —CO—O—, —O—CO— and —CH=CH—.

It is preferred that the groups S$^1$ to S$^3$ are selected from a single covalent bond, —O—, —CO—O—, —O—CO—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C—, —O—CO—O— and a straight-chain or branched alkylene group, which is optionally substituted by one or more groups selected from fluorine, chlorine and cyano and in which two or three non-adjacent alkylene —CH$_2$— group are independently optionally replaced by a group selected from —O—, —CO—O—, —O—CO—, —NR$^1$—, —NR$^1$—CO—, —CO—NR$^1$—, —NR$^1$—CO—O—, —O—CO—NR$^2$—, —NR$^1$—CO—NR$^1$—, —CH=CH—, —C≡C—, —O—CO—O— and —Si(CH$_3$)$_2$—O—Si(CH$_3$)$_2$—, wherein R$^1$ is as defined above and with the proviso that firstly, the total number of chain carbon atoms in the alkylene group does not exceed 24 and secondly, when the repeating monomer unit M is linked to B$^4$ via a nitrogen atom or a oxygen atom S$^1$, S$^2$ and S$^3$ are not —O—, —CO—O—, —O—CO—, —NR$^1$—, —NR$^1$—CO—, —CO—NR$^1$—, —NR$^1$—CO—O—, —CO—NR$^1$—, —NR$^1$—CO—NR$^1$—, —CH=CH—, —C≡C— or —O—CO—O—.

It is more preferred that S$^1$ to S$^3$ are selected from —CO—O—, —O—CO—, —(CH$_2$)$_r$—, —(CH$_2$)$_r$—O—, —(CH$_2$)$_r$—CO—, —(CH$_2$)$_r$—CO—O—, —(CH$_2$)$_r$—O—CO—, —(CH$_2$)$_r$—CO—NR$^1$—, —(CH$_2$)$_r$—NR$^1$—CO—, —(CH$_2$)$_r$—NR$^1$—, —O—(CH$_2$)$_r$—, —CO—O—(CH$_2$)$_r$—, —O—CO—(CH$_2$)$_r$—, —NR$^1$—CO—(CH$_2$)$_r$—, —CO—NR$^1$—(CH$_2$)$_r$—, —NR$^1$—(CH$_2$)$_r$—, —O—(CH$_2$)$_r$—CO—O—, —O—(CH$_2$)$_r$—O—CO—, —O—(CH$_2$)$_r$—CO—NR$^1$—, —O—(CH$_2$)$_r$—NR$^1$—, —O—(CH$_2$)$_r$—O—, —O—(CH$_2$)$_r$NR$^1$—CO—, —NR$^1$—(CH$_2$)$_r$—CO—O—, —NR$^1$—(CH$_2$)$_r$—O—, —NR$^1$—(CH$_2$)$_r$—NR$^1$—, —NR$^1$—(CH$_2$)$_r$—O—CO—, —CO—NR$^1$—(CH$_2$)$_r$—O—, —CO—NR$^1$—(CH$_2$)$_r$—NR$^1$—, —CO—NR$^1$—(CH$_2$)$_r$—O—CO—, —O—CO—(CH$_2$)$_r$—CO—, —O—CO—(CH$_2$)$_r$—O—, —O—CO—(CH$_2$)$_r$—NR$^2$—, —O—CO—(CH$_2$)$_r$—CO—O—, —O—CO—(CH$_2$)$_r$—CO—NR$^1$—, —O—CO—(CH$_2$)$_r$—NR$^1$—CO—, —(CH$_2$)$_r$—O—(CH$_2$)$_s$—, —(CH$_2$)$_r$—CO—O—(CH$_2$)$_s$—, —(CH$_2$)$_r$—O—CO—(CH$_2$)$_s$—, —(CH$_2$)$_r$—NR$^1$—CO—(CH$_2$)$_s$—, —(CH$_2$)$_r$—NR$^1$—CO—O—(CH$_2$)$_s$—, —(CH$_2$)$_r$—O—(CH$_2$)$_s$—O—, —(CH$_2$)$_r$—CO—O—(CH$_2$)$_s$—O—, —(CH$_2$)$_r$—O—CO—(CH$_2$)$_s$—O—, —(CH$_2$)$_r$—NR$^1$—CO—(CH$_2$)$_s$—O—, —(CH$_2$)$_r$—NR$^1$—CO—O—(CH$_2$)$_s$—O—, —O—(CH$_2$)$_r$—O—(CH$_2$)$_s$—, —O—(CH$_2$)$_r$—CO—O—(CH$_2$)$_s$—, —O—(CH$_2$)$_r$—NR$^1$—CO—(CH$_2$)$_s$—, —O—(CH$_2$)$_r$—NR$^1$—CO—O—(CH$_2$)$_s$—, —O—(CH$_2$)$_r$—COO—(CH$_2$)$_s$—O—, —O—(CH$_2$)$_r$—O—(CH$_2$)$_s$—O—, —O—(CH$_2$)$_r$—NR$^1$—CO—(CH$_2$)$_s$—O—, —O—(CH$_2$)$_r$—NR$^1$—CO—O—(CH$_2$)$_s$—O—, —CO—O—(CH$_2$)$_r$—O—(CH$_2$)$_s$— and —CO—O—(CH$_2$)$_r$—O—(CH$_2$)$_s$—O—, wherein R$^1$ is as defined above, r and s each represent an integer from 1 to 20, preferably from 2 to 12, and r+s≦21, preferably ≦15.

By the terms —(CH$_2$)$_r$— and —(CH$_2$)$_s$— it should be understood to include straight-chain or branched alkylene groupings containing r or s carbon atoms respectively. Optional substituents include alkyl, aryl, cycloalkyl, amino, cyano, epoxy, halogen, hydroxy, nitro and oxo.

It is especially preferred that S$^1$ to S$^3$ are selected from —(CH$_2$)$_r$—, —(CH$_2$)$_r$—O—, —(CH$_2$)$_r$—CO—O—, —(CH$_2$)$_r$—O—CO—, —(CH$_2$)$_r$—CO—NH—, —(CH$_2$)$_r$—NH—CO—, —O—(CH$_2$)$_r$—, —CO—O—(CH$_2$)$_r$—, —CO—NH—(CH$_2$)$_r$—, —O—CO—(CH$_2$)$_r$—, —O—CO—(CH$_2$)$_r$—CO—O—, —O—(CH$_2$)$_r$—O—CO—, —O(CH$_2$)$_r$—CO—NH—, —O—(CH$_2$)$_r$—NH—CO—, —CO—O—(CH$_2$)$_r$—O—, —CO—NH—(CH$_2$)$_r$—O—, —O—(CH$_2$)$_r$—O—, —(CH$_2$)$_r$—NH—CO—(CH$_2$)$_s$—, —(CH$_2$)$_r$—NH—CO—O—(CH$_2$)$_s$—, —(CH$_2$)$_r$—O—(CH$_2$)$_s$—O—, —(CH$_2$)$_r$—NH—CO—(CH$_2$)$_s$—O—, —(CH$_2$)$_r$—NH—CO—O—(CH$_2$)$_s$—O, —O—(CH$_2$)$_r$—NH—CO—(CH$_2$)$_s$—, —O—(CH$_2$)$_r$—O—(CH$_2$)$_s$—O—, —O—CO—(CH$_2$)$_r$—O—(CH$_2$)$_s$—O—, —CO—O—(CH$_2$)$_r$—O—(CH$_2$)$_s$—O—, —O—(CH$_2$)$_r$—NH—CO—(CH$_2$)$_s$—O— and —O—CO—(CH$_2$)$_r$—NH—CO—(CH$_2$)$_s$—O—, wherein r and s each represent an integer from 2 to 12 and r+s≦15.

Examples of preferred the preferred groups S$^1$ to S$^3$ include 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 3-methyl-1,4-butylene, 3-propyleneoxy, 3-propyleneoxycarbonyl, 2-ethylenecarbonyloxy, 4-butyleneoxy, 4-butyleneoxycarbonyl, 3propylenecarbonyloxy, 5-pentyleneoxy, 5-pentyleneoxycarbonyl, 4-butylenecarbonyloxy, 6-hexyleneoxy, 6-hexyleneoxycarbonyl, 5-pentylenecarbonyloxy, 7-heptyleneoxy, 7-heptyleneoxycarbonyl, 6-hexylenecarbonyloxy, 8-octyleneoxy, 8-octyleneoxycarbonyl, 7-heptylenecarbonyloxy, 9-nonyleneoxy, 9-nonyleneoxycarbonyl, 8-octylenecarbonyloxy, 10decyleneoxy, 10-decyleneoxycarbonyl, 9-nonylenecarbonyloxy, 11-undecylencoxy, 11-undecyleneoxycarbonyl, 10-decylenecaonyloxy, 12-dodecyleneoxy, 12-dodecyleneoxycarbonyl, 11-undecylenecarbonyloxy, 3-propyleneiminocarbonyl, 4-butyleneiminocarbonyl, 5-pentyleneiminocarbonyl, 6-hexyleneiminocarbonyl, 7-heptyleneiminocarbonyl, 8-octyleneiminocarbonyl, 9-nonyleneimiocarbonyl, 10-decyleneiminocarbonyl, 11-undecyleneiminocarbonyl, 12dodecyleneiminocarbonyl, 2-ethylenecarbonylumno, 3-propylenecarbonylimino, 4-butylenecarbonylimino, 5-pentylenecarbonylimino, 6-hexylenecarbonylimino, 7-heptylenecarbonylimino, 8-octylenecarbonylimino, 9-nonylenecarbonylinino, 10-decylenecarbonylimino, 11-undecylenecarbonylimino, 6-(3-propyleneimiocarbonyloxy)hexylene, 6-(3-propyleneoxy)hexylene, 6-(3-propyleneoxy)hexyleneoxy, 6(3-propyleneminocarbonyloxy)hexyleneoxy, 6-(3-propyleneiminocarbonyl)hexyl, 6-(3-propyleneiminocarbonyl)hexyloxy, 1,2-ethylenedioxy, 1,3-propylenedioxy, 1,4-butylenedioxy, 1,5-pentylenedioxy, 1,6-hexylenedioxy, 1,7-heptylenedioxy, 1,8-octylenedioxy, 1,9-nonylenedioxy, 1,10-decylenedioxy, 1,11-undecylenedioxy, 1,12-dodecylenedioxy and the like.

It is preferred that the unit of formula (I) comprises at least 50% of the monomer building blocks, which form the main chain of a photoactive polymer. It is especially preferred that the unit of formula (I) comprises at least 70% of the monomer building blocks forming the photoactive polymer.

The repeating monomer unit M represents part of a homopolymer or a co-polymer. It is preferred that M forms part of a co-polymer. By the term "copolymer" it is to be understood to include statistical copolymers.

The repeating monomer units M are preferably selected from acrylate; methacrylate; 2-chloroacrylate; 2-phenylacrylate; acrylamide, methacrylamide, 2-chloroarylamide and 2-phenylacrylamide, the nitrogen atom of which is optionally substituted by a lower alkyl group; vinyl ether; vinyl ester, a styrene derivative; siloxane; imide; amic acid; amic acid esters; amidimide; maleic acid derivatives and fumaric acid derivatives.

It is more preferred that the repeating monomer unit M is selected from acrylate; methacrylate; acrylamide and methacrylamide the nitrogen atom of which is optionally substituted by a lower alkyl group; vinyl ether, vinyl ester, a styrene derivative, imide, amic acid, amic acid esters and amidimide.

It is especially preferred that the repeating monomer unit M is selected from acrylate, methacrylate, a styrene derivative, imide, amic acid, amic acid ester, and amidimide.

When the monomer unit M is an imide group, it is preferably selected from structures of the general formulae VI, VII, VIII, IX, X and XI:

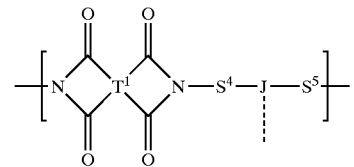

VI

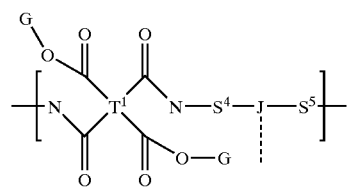

VII

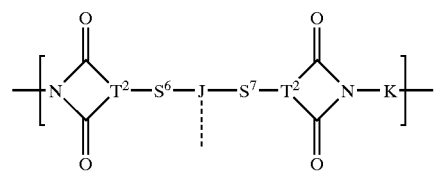

VIII

-continued

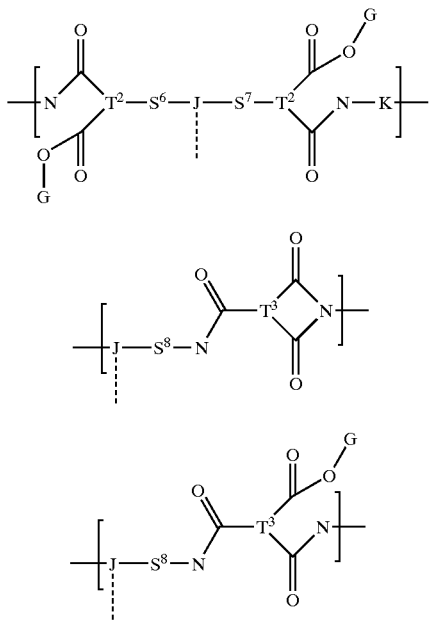

IX

X

XI wherein the broken line symbolises the linkage to $B^4$ $T^1$ represents a tetravalent organic radical;

$T^2$, $T^3$ each independently represent a trivalent aromatic or alicyclic group which is optionally substituted by a group selected from fluorine, chlorine, cyano and a $C_{1-18}$ cyclic, straight-chain or branched alkyl residue, which is optionally substituted by one or more halogen groups and in which one or more non-adjacent alkyl —$CH_2$— groups are independently optionally replaced by a group selected from —O—, —CO—, —CO—O—, —O—CO—, —CH=CH— and —C≡C—, $S^4$ to $S^8$ are each independently selected from a single covalent bond and a $C_{1-24}$ straight-chain or branched alkylene residue, which is optionally substituted by a single cyano group or by one or more halogen atoms and in which one or more non-adjacent alkylene —$CH_2$— groups are, independently, optionally replaced by a group selected from —O—, —CO—, —CO—O—, —O—CO, —Si$(CH_3)_2$—O—Si$(CH_3)_2$—, —$NR^1$—, —$NR^1$—CO—, —CO—$NR^1$—, —$NR^1$—CO—O—, —O—CO—$NR^1$—, —$NR^1$—CO—$NR^1$—, —CH=CH—, —C≡C— and —O—CO—O—, wherein $R^1$ is as defined above;

J is selected from the group comprising a nitrogen atom, a group —$CR^1$— and an aromatic or alicyclic divalent, trivalent or tetravalent group, which is optionally substituted by one or more groups selected from fluoro, chloro, cyano and a $C_{1-18}$ cyclic, straight-chain or branched alkyl residue which is optionally substituted by a single cyano group or by one or more halogen atoms and in which one or more non-adjacent —$CH_2$— groups are, independently, optionally, replaced by a group selected from —O—, —CO—, —CO—O—, —O—CO—, —CH=CH— and —C≡C— wherein $R^1$ is as defined above;

K represents an aliphatic, alicyclic or aromatic divalent radical; and

G represents a hydrogen atom or a monovalent organic group.

By the term "aliphatic" it should be understood to include saturated and unsaturated, straight-chain and branched alkyl groups, which may be optionally substituted and in which one or more non-adjacent —$CH_2$— groups are replaced by one or more heteroatoms. Optional substituents include alkyl, aryl, cycloalkyl, amino, cyano, epoxy, halogen, hydroxy, nitro and oxo. Examples of heteroatoms that can replace the one or more —$CH_2$— groups include nitrogen, oxygen and sulfur. Replacement nitrogen atoms may be further substituted with groups such as alkyl, aryl and cycloalkyl.

The tetravalent organic radical $T^1$ is preferably derived from an aliphatic, alicyclic or aromatic tetracarboxylic acid dianhydride. Alicyclic or aliphatic tetracarboxylic acid anhydrides are preferably selected from butanetetracarboxylic acid dianhydride, ethylenemaleic acid dianhydride, 1,2,3,4-cyclobutanetetracarboxylic acid dianhydride, 1,2,3,4-cyclopentanetetracarboxylic acid dianhydride, 2,3,5-tricarboxycyclopentylacetic acid dianhydride, 3,5,6-tricarboxynorbornylacetic acid dianhydride, 2,3,4,5-tetrahydrofurantetracarboxylic acid dianhydride, 4-(2,5-dioxotetrahydrofuran-3-yl)tetrahydronaphthalene-1,2-dicarboxylic acid dianhydride, 5-(2,5-dioxotetrahydrofuran-3-yl)-3-methyl-3-cyclohexene-1,2-dicarboxylic acid dianhydride, bicyclo[2.2.2]oct-7-ene-2,3,5,6-tetracarboxylic acid dianhydride, bicyclo[2.2.2]octane-2,3,5,6-tetracarboxylic acid dianhydride and 1,8-dimethylbicyclo[2.2.2]oct-7-ene-2,3,5,6-tetracarboxylic acid dianhydride.

Aromatic tetracarboxylic acid dianhydrides are preferably selected from pyromellitic acid dianhydride, 3,3',4,4'-benzophenonetetracarboxylic acid dianhydride, 4,4'-oxydiphthalic acid dianhydride, 3,3',4,4'-diphenylsulfonetetracarboxylic acid dianhydride, 1,4,5,8-naphthalenetetracarboxylic acid dianhydride, 2,3,6,7-naphthalenetetracarboxylic acid dianhydride, 3,3',4,4'-dimethyldiphenylsilanetetracarboxylic acid dianhydride, 3,3',4,4'-tetraphenylsilanetetracarboxylic acid dianhydride, 1,2,3,4-furantetracarboxylic acid dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4dicarboxyphenoxy)diphenylpropane dianhydride, 3,3',4,4'-biphenyltetracarboxylic acid dianhydride, ethylene glycol bis(trimellitic acid) dianhydride, 4,4'-(1,4-phenylene) bisphthalic acid) dianhydride, 4,4'-(1,3-phenylene)bis (phthalic acid) dianhydride, 4,4'-(hexafluoroisopropylidene) diphthalic acid dianhydride, 4,4'-oxydi(1,4-phenylene)bis (phthalic acid) dianhydride and 4,4'-methylenedi(1,4-phenylene)bis(phthalic acid) dianhydride.

It is especially preferred that the tetracarboxylic acid dianhydrides used to form the tetravalent organic radical $T^1$ are selected from 1,2,3,4-cyclobutanetetracarboxylic acid dianhydride, 1,2,3,4-cyclopentanetetracarboxylic acid dianhydride, 2,3,5-tricarboxycyclopentylacetic acid dianhydride, 5-(2,5-dioxotetrahydrofuran-3-yl)-3-methyl-3-cyclohexene-1,2-dicarboxylic acid dianhydride, 4-(2, 5dioxotetrahydrofuran-3-yl)tetrahydronaphthalene-1,2-dicarboxylic acid dianhydride, 4,4'-(hexafluoroisopropylidene)diphthalic acid dianhydride and bicyclo[2.2.2]oct-7-ene-2,3,5,6-tetracarboxylic acid dianhydride.

Each of the groups $T^2$ and $T^3$ can be derived from an aliphatic, alicyclic or aromatic dicarboxylic acid anhydride.

The groups $T^2$ and $T^3$ are preferably trivalent aromatic or alicyclic groups, the three valencies of which are distributed between three different carbon atoms, with the proviso that two of the valencies are located at adjacent carbon atoms. It is especially preferred that the groups $T^2$ and $T^3$ are trivalent benzene derivatives.

The group $S^4$ is preferably selected from a single covalent bond, —$(CH_2)_r$—, —$(CH_2)_r$—O—, —$(CH_2)_r$—CO—, —$(CH_2)_r$—CO—O—, —$(CH_2)_r$—O—CO—, —$(CH_2)_r$—CO—$NR^1$—, —$(CH_2)_r^1$—CO—, —$(CH_2)_r$—$NR^1$—, —$(CH_2)_r$—O—$(CH_2)_s$—, —$(CH_2)_r$—CO—O—$(CH_2)_s$—, —$(CH_2)_r$—O—CO—$(CH_2)_s$—, —$(CH_2)_r$—$NR^1$—CO—$(CH_2)_s$—, —$(CH_2)_r$—$NR^1$—CO—O—$(CH_2)_s$—, —$(CH_2)_r$—O$(CH_2)_s$—O—, —$(CH_2)_r$—CO—O—$(CH_2)_s$—O—, —$(CH_2)_r$—O—OC—$(CH_2)_s$—O—, —$(CH_2)_r$—$NR^1$—CO—$(CH_2)_s$—O—, —$(CH_2)_r$—$NR^1$—CO—O—$(CH_2)_s$—O—, —$(CH_2)_r$—O—$(CH_2)_s$—CO—O— and —$(CH_2)_r$—O—$(CH_2)_s$—O—CO—, wherein $R^1$ is as defined herein above; r and s each represent an integer from 1 to 20; and r+s≦21. It is more preferred that r and s each represent an integer from 2 to 12. It is especially preferred that r+s≦15.

Examples of preferred groups $S^4$ include 1,2-ethylene, 1,3-propylene, 1,4-butylene, 1,5-pentylene, 1,6hexylene, 1,7-heptylene, 1,8-octylene, 1,9-nonylene, 1,1-decylene, 1,11-undecylene, 1,12-dodecylene, 3-methyl-1,4-butylene, 3-propyleneoxy, 3-propyleneoxycarbonyl, 2-ethylenecarbonyloxy, 4-butyleneoxy, 4-butyleneoxycarbonyl, 3-propylenecarbonyloxy, 5-pentyleneoxy, 5-pentyleneoxycarbonyl, 4-butylenecarbonyloxy, 6-hexyleneoxy, 6-hexyleneoxycarbonyl, 5-pentylenecarbonyloxy, 7-heptyleneoxy, 7-heptyleneoxycarbonyl, 6-hexylenecarbonyloxy, 8-octyleneoxy, 8-octyleneoxycarbonyl, 7-heptylenecarbonyloxy, 9-nonyleneoxy, 9-nonyleneoxycarbonyl, 8-octylenecarbonyloxy, 10-decyleneoxy, 10-decyleneoxycarbonyl, 9-nonylenecarbonyloxy, 11-undecyleneoxy, 11-undecyleneoxycarbonyl, 10-decylenecarbonyloxy, 12-dodecyleneoxy, 12-dodecyleneoxycarbonyl, 11-undecylenecarbonyloxy, 3-propyleneocarbonyl, 4-butyleiminocarbonyl, 5-pentyleneiminocarbonyl, 6-hexyleneiminocarbonyl, 7-heptyleneiminocarbonyl, 8-octyleneiminocarbonyl, 9-nonylenemocarbonyl, 10-decyleneiminocarbonyl, 11-undecyleneiminocarbonyl, 12-dodecyleneiminocarbonyl, 2-ethylenecarbonylimino, 3-propylenecarbonylimino, 4-butylenecarbonylimino, 5-pentylenecarbonylimino, 6-hexylenecarbonylimino, 7-heptylenecarbonylimino, 8-octylenecarbonylimino, 9-nonylemecarbonylimino, 10-decylenecarbonylimino, 11-undecylenecarbonylimino, 6-(3-propylene-iminocarbonyloxy)hexylene, 6-(3-propyleneoxy)hexylene, 6-(3-propyleneoxy)hexyleneoxy, 6-(3-propylene-iminocarbonyloxy)hexyleneoxy, 6-(3-propylene-iminocarbonyl)hexylene, 6-(3-propyleneiminocarbonyl)hexyleneoxy and the like.

The groups $S^5$ and $S^8$ are preferably selected from a single bond, —$(CH_2)_r$—, —O—$(CH_2)_r$—, —CO—$(CH_2)_r$—, —CO—O—$(CH_2)_r$—, —O—CO—$(CH_2)_r$—, —$NR^1$—CO—$(CH_2)_r$—, —$NR^1$—$(CH_2)_r$—, —CO—$NR^1$—$(CH_2)_r$—, —$NR^1$—CO—$(CH_2)_r$—, —O—$(CH_2)_r$—O—$(CH_2)_s$—, —$(CH_2)_r$—CO—O—$(CH_2)_s$—, —$(CH_2)_r$—O—CO—$(CH_2)_s$—, —$(CH_2)_r$—$NR^1$—CO—$(CH_2)_s$—, —$(CH_2)_r$—$NR^1$CO—O—$(CH_2)_s$—, —O—$(CH_2)_r$—O—$(CH_2)_s$—, —O—$(CH_2)_r$—CO—O—$(CH_2)_s$—, —$(CH_2)_r$—O—CO—$(CH_2)_s$, —O—$(CH_2)_r$—O—CO—$(CH_2)_s$, —O—$(CH_2)_r$—$NR^1$—CO—$(CH_2)_s$, —O—$(CH_2)_r$—$NR^1$CO—O—$(CH_2)_s$—, —O—CO—$(CH_2)_r$—O—$(CH_2)_s$— and —CO—O—$(CH_2)_r$—O—$(CH_2)_s$—, wherein $R^1$ is defined as herein above; r and s each represent an integer from 1 to 20; and r+s≦21. It is more preferred that r and s each represent an integer from 2 to 12. It is further preferred that r+s≦15.

Examples of preferred groups $S^5$ and $S^8$ include 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 3-methyl-1,4-butylene, 2-oxyethylene, 3-oxypropylene, 4-oxybutylene, 5-oxypentylene, 6-oxyhexylene, 7-oxyheptylene, 8-oxyoctylene, 9-oxynonylene, 10-oxydecylene, 11-oxyundecylene, 12-oxydodecylene, 2-(oxycarbonyl)ethylene, 3-(oxycarbonyl)propylene, 4-(oxycarbonyl)butylene, 5-oxycarbonyl)pentylene, 6-(oxycarbonyl)hexylene, 7-(oxycarbonyl)heptylene, 5-(oxycarbonyloctylene, 9-(oxycarbonyl)nonylene, 10-(oxycarbonyl)decylene, 11-(oxycarbonyl)undecylene, 12-(oxycarbonyl)dodecylene, 2-(carbonyloxy)ethylene, 3carbonyloxy)propylene, 4-(carbonyloxy)butylene, 5-(carbonyloxypentylene, 6-(carbonyloxy)hexylene, 7carbonyloxy)heptylene, 8-(carbonyloxy)octylene, 9-(carbonyloxy)nonylene, 10-(carbonyloxy)decylene, 11-(carbonyloxy)undecylene, 12-(carbonyloxy)dodecylene, 2-(carbonylimino)ethylene, 3-(carbonylimino)propylene, 4(carbonylimino)butylene, 5-(carbonylimino)pentylene, 6-(carbonylimno)hexylene, 7-(carbonylimino)heptylene, 8-(carbonylimo)octylene, 9-(carbonylimino)nonylene, 10-(carbonylimino)decylene, 11-(carbonylimino)undecylene, 12-(carbonylimino)dodecylene, 2-iminoethylene, 11-iminopropylene, 4-iminobutylene, 5-iminopentylene, 6-iminohexylene, 7-iminoheptylene, 8-iminooctylene, 9-iminononylene, 10-iminodecylene, 11-iminoundecylene, 12-iminododecylene, 2-imiocarbonylethylene, 3-iminocarbonylpropylene, 3-iminocarbonylbutylene, 5-iminocarbonylpentylene, 6-iminocarbonylhexylene, 7-iminocarbonylheptylene, 8-iminocarbonyloctylene, 9-iminocarbonylnonylene, 10-iminocarbonyldecylene, 11-iminocarbonylundecylene, 12-iminocarbonyl-dodecylene, 2-(2-ethyleneoxy)ethylene, 2-(3-propyleneoxy)ethylene, 6-(4butyleneoxy)hexylene, 2-(2-ethylene-iminocarbonyl)ethylene, 2-(3-propyleneiminocarbonyl)ethylene, 6-(4-butyleneiminocarbonyl)hexylene, 6-(3-propyleneiminocarbonyloxy)hexylene, 6-(3-propylene-iminocarbonyl)hexylene and the like.

The groups $S^6$ and $S^7$ are preferably selected from a single bond, —$(CH_2)_r$—, —$(CH_2)_r$—O—, —$(CH_2)_r$—CO—, —$(CH_2)_r$—CO—O—, —$(CH_2)_r$—O—CO—, —$(CH_2)_r$—CO—$NR^1$—, —$(CH_2)_r$—$NR^1$—CO—, —$(CH_2)_r$—$NR^1$, —O—$(CH_2)_r$—, —CO—O—$(CH_2)_r$—, —O—CO—$(CH_2)_r$—, —$NR^1$—CO—$(CH_2)_r$, —CO—$NR^1$—$(CH_2)_r$—, —$NR^1$—$(CH_2)_r$—, —O—$(CH_2)_r$—CO—O—, —O—$(CH_2)_r$—O—CO—, —O—$(CH_2)_r$—CO—$NR^1$—, —O—$(CH_2)_r$—$NR^1$—, —O—$(CH_2)_r$—O—, —O—$(CH_2)_r$—$NR^1$—CO—, —$NR^1$—$(CH_2)_r$—CO—O—, —$NR^1$—$(CH_2)_r$—O—, —$NR^1$—$(CH_2)_r$—$NR^1$—, —$NR^1$—$(CH_2)_r$—O—CO—, —CO—$NR^1$$(CH_2)_r$—O—, —CO—$NR^1$—$(CH_2)_r$—$NR^1$—, —CO—$NR^1$—$(CH_2)_r$—O—CO—, —O—CO$(CH_2)_r$—CO—, —O—CO—$(CH_2)_r$—O—, —O—CH—$(CH_2)_r$—$NR^1$—, —O—CO—$(CH_2)_r$—CO—O—, —O—CO—$(CH_2)_r$—CO—$NR^1$—, —O—CO—$(CH_2)_r$—$NR^1$—CO—, —$(CH_2)_r$—O—$(CH_2)_s$—, —$(CH_2)_r$—CO—O—$(CH_2)_s$—, —$(CH_2)_r$—O—CO—$(CH_2)_s$—, —$(CH_2)_r$—$NR^1$—CO—$(CH_2)_s$—, —$(CH_2)_r$—$NR^1$—CO—O—$(CH_2)_s$—, —$(CH_2)_r$—O—$(CH_2)_s$—O—, —$(CH_2)_r$—CO—O—$(CH_2)_s$—O—, —$(CH_2)_r$—O—CO—$(CH_2)_s$—O—, —$(CH_2)_r$—$NR^1$—CO—$(CH_2)_s$—O—, —$(CH_2)_r$—$NR^1$—CO—O—$(CH_2)_s$—O—, —O—$(CH_2)_r$—O—$(CH_2)_s$—, —O—$(CH_2)_r$—CO—O—$(CH_2)_s$—, —O—$(CH_2)_r$—$NR^1$—CO—$(CH_2)_s$—, —O—$(CH_2)_r$—$NR^1$—CO—O—$(CH_2)_s$—, —O—$(CH_2)_r$—CO—O—$(CH_2)_s$—O—, —O—$(CH_2)_r$—O—

$(CH_2)_s$—O—, —O—$(CH_2)_r$—$NR^1$—CO—$(CH_2)_s$—O—, —O—$(CH_2)_r$—$NR^1$—CO—O—$(CH_2)_s$—O—, —CO—O—$(CH_2)_r$—O—$(CH_2)_s$—, —CO—O—$(CH_2)_r$—O—$(CH_2)_s$—O—, wherein $R^1$ is defined as herein above; r and s each represent an integer from 1 to 20; and +s≦21. It is more preferred that r and s each represent an integer from 2 to 12. It is especially preferred that r+s ≦15.

Examples of preferred groups $S^6$ and $S^7$ include 1,2-ethylene, 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 3-methyl-1,4-butylene, 3-propyleneoxy, 3-propyleneoxycarbonyl, 2-ethylenecarbonyloxy, 4-butyleneoxy, 4-butyleneoxycarbonyl, 3-propylenecarbonyloxy, 5-pentyleneoxy, 5-pentyleneoxycarbonyl, 4-butylenecarbonyloxy, 6-hexyleneoxy, 6-hexyleneoxycarbonyl, 5-pentylenecarbonyloxy, 7-heptyleneoxy, 7-heptyleneoxycarbonyl, 6-hexylenecarbonyloxy, 8-octyleneoxy, 8-octyleneoxycarbonyl, 7-heptylenecarbonyloxy, 9-nonyleneoxy, 9-nonyleneoxycarbonyl, 9-octylenecarbonyloxy, 10-decyleneoxy, 10-decyleneoxycarbonyl, 9-nonylenecarbonyloxy, 11-undecyleneoxy, 11-undecyleneoxycarbony, 10-decylenecarbonyloxy, 12-dodecyleneoxy, 12-dodecyleneoxycarbonyl, 11-undecylenecarbonyloxy, 3-propyleneiminocarbonyl, 4-butyleneiminocarbonyl, 5-pentyleneiminocarbonyl, 6-hexyleneiminocarbonyl, 7-heptyleneiminocarbonyl, 8-octyleneiminocarbonyl, 9-nonyleneiminocarbonyl, 10-decyleneiminocarbonyl, 11-undecyleneiminocarbonyl, 12-dodecyleneiminocarbonyl, 2-ethylenecarbonylimino, 3-propylenecarbonylimino, 4-butylenecarbonylimino, 5-pentylenecarbonylimino, 6-hexylenecarbonylimino, 7-heptylenecarbonylimino, 8-octylenecarbonylimino, 9-nonylemecarbonylimino, 10-decylenecarbonylimino, 11-undecylenecarbonylimino, 6-(3-propylene-iminocarbonyloxy)hexylene, 6(3-propyleneoxy)hexylene, 6-(3-propyleneoxy)hexyleneoxy, 6-(3-propylene-iminocarbonyloxy)hexyleneoxy, 6-(3-propylene-iminocarbonyl)hexyl, 6-(3-propyleneiminocarbonyl)hexyloxy, 1,2-ethylenedioxy, 1,3-propylenedioxy, 1,4-butylenedioxy, 1,5-pentylenedioxy, 1,6-hexylenedioxy, 1,7-heptylenedioxy, 1,8-octylenedioxy, 1,9-nonylenedioxy, 1,10-decylenedioxy, 1,11-undecylenedioxy, 1,12-dodecylenedioxy and the like.

The aliphatic, alicyclic or aromatic divalent radical K is derivable from aliphatc, alicyclic or aromatic diamines by formal removal of the amino groups. Examples of aliphatic or alicyclic diamines from which the radical K can be derived include ethylenediamine, 1,3-propylenediamine, 1,4-butylenediamine, 1,5-pentylenediamine, 1,6-hexylenediamine, 1,7-heptylenediamine, 1,8-octylenediamine, 1,9-nonylenediamine, 1,10decylenediamine, 1,11-undecylenediamine, 1,12-dodecylenediamie, α,α'-diamino-m-xylene, α,α'-diamino-p-xylene, (5-amino-2,2,4-trimethylcyclopentyl) methylamine, 1,2-diaminocyclohexane, 4,4'-diaminodicyclohexylmethane, 1,3-bis(methylamino) cyclohexane, and 4,9-dioxadodecane-1,12-diamine.

Examples of aromatic diamines from which the radical K can be derived include 3,5-diaminobenzoic acid methyl ester, 3,5-diaminobenzoic acid hexyl ester, 3,5-diaminobenzoic acid dodecyl ester, 3,5-diaminobenzoic acid isopropyl ester, 4,4'-methylenedianiline, 4,4'-ethylenedianiline, 4,4'-diamino-3,3'-dimethyl-diphenylmethane, 3,3',5,5'-tetramethylbenzidine, 4,4'-diaminodiphenyl sulfone, 4,4'-diaminodiphenyl ether, 1,5-diaminonaphthalene, 3,3'-dimethyl-4,4'-diaminobiphenyl, 3,4'-diaminodiphenyl ether, 3,3'-diaminobenzophenone, 4,4'-diaminobenzophenone, 4,4'-diamino-2,2'-dimethylbibenzyl, 2,2-bis[4(4aminophenoxy) phenyl]sulfone, 1,4-bis(4aminophenoxy)benzene, 1,3-bis (4aminophenoxy)benene, 1,3-bis(3-aminophenoxy) benzene, 2,7-diaminofluorene, 9,9-bis(4-aminophenyl) fluorene, 4,4'-methylenebis(2-chloroaniline), 4,4-bis (4amiophenoxy)biphenyl, 2,2',5,5'-tetrachloro-4,4'-2,2'-dichloro-4,4'-diamino-5,5'- diethoxybiphenyl, 3,3'-diethoxy-4,4'-diaminobiphenyl 4,4'-(1,4-phenyleneisopropylidene)bisenile, 4,4'-(1,3-phenyleneisopropylidene)bisaniline, 2,2-bis[4(4-aminophenoxy)phenyl]-propane, 2,2-bis[3-(4aminophenoxyphenyl]hexafluoropropane, 2,2-bis[3-amino-4-methylphenyl]hexafluoropropane, 2,2-bis (4aminophenyl)hexafluoropropane, 2,2'-bis[4(4-amino-2-trifluoromethylphenoxy)phenyl]hexafluoropropane, 4,4'-diamino-2,2'-bis(trifluoromethyl)biphenyl, and 4,4'-bis[(4-amino-2-trifluoromethyl)phenoxy]-2,3,5,6,2',3',5',6'-octafluorobiphenyl.

The group J may be divalent, trivalent or tetravalent. When J is divalent, it serves to link the groups $S^4$ and $S^5$, $S^6$ and $S^7$ and $S^8$ and N respectively of the groups VI to XI, It will be appreciated that when J is a divalent group, the monomer unit of which it forms a part is not linked to a side chain group $B^4$. When J is a trivalent or a tetravalent group, it serves to link the monomer unit M, of which it forms a part, to one or two side chain groups $B^4$ respectively. It is preferred that the photoactive polymer comprises less than 75%, of monomer units including a divalent group J, preferably less than 50% and especially less than 30%. Monomer units M comprising a trivalent group J are preferred.

The building blocks of the formulae VII, IX and XI are amic acid groupings or amic acid ester groupings (i.e. carboxamide-carboxylic acid groupings or carboxamide-carboxylic acid ester groupings) which on the one hand may occur as a result of incomplete imidisation in the polyimide chain. On the other hand, polymers that consist only of building blocks of formulae VII, IX or XI, that is to say polyamic acids or polyamic acid esters, are important precursors for the preparation of the polyimides according to the invention and are also included in the present invention. Of those polymers which contain groups of formulae VII, IX or XI, preference is given to those in which G is hydrogen, that is to say those which consist exclusively of, or contain some, polyamic acid groups.

The polymers of the invention may be prepared using methods that are known to a person skilled in the art and a second aspect of the invention provides a method of preparing a compound of formula (I) as defined above.

The polymers of formula I, with acrylate, methacrylate and styrene derivative as repeating monomer unit, can be prepared in principle according to two different processes. In addition to the direct polymerisation of pre-finished monomers there exists the possibility of polymer-analogous reaction of reactive photoactive all derivatives with functional polymers.

For the direct polymerisation, the monomers and the comonomers are firstly prepared separately from the individual components. The formation of the polymers is subsequently effected in a manner known per se under the influence of UV radiation or heat or by the action of radical or ionic catalysts. Potassium peroxodisulfate, dibenzoyl peroxide, azobisisobutyronitrile or di-tert-butyl peroxide are examples of radical initiators. Ionic catalysts are alkali-organic compounds such as phenyllithium or naphthylsodium or Lewis acids such as $BF_3$, $AlCl_3$, $SnCl_3$ or $TiCl_4$. The monomers can be polymerised in solution, suspension, emulsion or substance.

In the second process a polymer of formula I can also be produced in a polymer-analogous reaction from a prefinished functional polymer and a suitable functionalised photoactive derivative. Many known processes such as, for example, esterification, trans-esterification, amidation or the etherification are suitable for polymer-analogous reactions.

Acrylate, methacrylate and styrene polymers typically have a molecular weight $M_W$ of from 1 000 to 5 000 000, preferably from 5 000 to 2 000 000, and especially from 10 000 to 1 000 000.

Polyamic acids and polyimides of the present invention may be prepared in accordance with known methods, such as those described in *Plast. Eng.* 36 (1996) (Polyimides, fundamentals and applications).

For example, the polycondensation reaction for the preparation of the polyamic acids is carried out in solution in a polar aprotic organic solvent, such as γ-butyrolactone, N,N-dimethylacetamide, N-methylpyrrolidone or N,N-dimethylformamide. In most cases equimolar amounts of the dianhydride and the diamine are used, that is to say one amino group per anhydride group. If it is desired to stabilise the molecular weight of the polymer, it is possible for that purpose to add an excess or a less-than-stoichiometric amount of one of the two components or to add a monofunctional compound in the form of a dicarboxylic acid monoanhydride or in the form of a monoamine. Examples of such monofunctional compounds are maleic acid anhydride, phthalic acid anhydride, aniline and so on. The reaction is carried out preferably at a temperature of less than 100° C.

The cyclisation of the polyamic acids to form the polyimides can be carried out by heating, that is to say by condensation with removal of water or by other imidisation reactions with reagents. When carried out purely thermally, the imidisation of the polyamic acids is not always complete, that is to say the resulting polyimides may still contain proportions of polyanic acid. The imidisation reactions are generally carried out at a temperature of from 60 to 250° C., but preferably at less than 200° C. In order to achieve imidisation at rather lower temperatures there are additionally mixed into the reaction mixture reagents that facilitate the removal of water. Such reagents are, for example, mixtures consisting of acid anhydrides, such as acetic acid anhydride, propionic acid anhydride, phthalic acid anhydride, trifluoroacetic acid anhydride, and tertiary amines, such as triethylaine, trimethylamine, tributylamine, pyridine, N,N-dimethylaniline, lutidine, collidine etc., The amount of reagents used in that case is preferably at least two equivalents of amine and four equivalents of acid anhydride per equivalent of polyamic acid to be condensed.

The imidisation reaction can be carried out before or alternatively only after application to a support. The latter variant is preferred especially when the polyimide in question has poor solubility in the customary solvents.

The polyamic acids and the polyimides of the present invention have an intrinsic viscosity preferably in range of 0.05 to 10 dL/g, more preferably 0.05 to 5 dL/g. Herein, the intrinsic viscosity ($\eta_{inh}=\ln \eta_{rel}/C$) is determined by measuring a solution containing a polymer in a concentration of 0.5 g/100 ml for its viscosity at 30° C. using N-methyl-2-pyrrolidone as solvent.

The polyamic acid chains or polyimide chains of the present invention preferably contain from 2 to 2000 monomer units, especially from 3 to 200.

Additives such as silane-containing compounds and epoxy-containing crosslinking agents may be added to the polymers of the invention in order to improve the adhesion of the polymer to a substrate. Suitable silane-containing compounds are described in *Plast. Eng.* 36 (1996) (Polyimides, fundamentals and applications). Suitable epoxy-containing crosslinking agents include 4,4'-methylenebis-(N,N-diglycidylaniline), timethylolpropane triglycidyl ether, benzene-1,2,4,5-tetracarboxylic acid 1,2:4,5-N,N'-diglycidyldiimide, polyethylene glycol diglycidyl ether, N,N-diglycidylcyclohexylamine and the like.

Further additives such a photosensitiser, a photoradical generator and/or a cationic photoinitiator may also be added to the polymers of the invention. Suitable photoactive additives include 2,2-dimethoxyphenylethanone, a mixture of diphenylmethanone and N,N-dimethylbenzenamine or ethyl-4-(dimethylamino)benzoate, xanthone, thioxanthone, Irgacure™ 184, 369, 500, 651 and 907 (Ciba), Michler's ketone, triarl sulfonium salt and the like.

The polymers according to the invention may be used alone or in combination with other polymers, oligomers, monomers, photoactive polymers, photoactive oligomers and/or photoactive monomers, depending up on the application to which the polymer layer is to be put. It will therefore be appreciated that by varying the composition of the polymer layer it is possible to control properties such as an induced pretilt angle, good surface wetting, high voltage holding ratio, a specific anchoring energy etc.

Polymer layers may be readily prepared from the polymers of the present invention and a third aspect of the invention provides a polymer layer comprising a polymer according to the present invention in a cross-linked form. The polymer layer is preferably prepared by applying one or more polymers according to the invention to a support and, after any imidisation step which may be necessary, crosslinkig the polymer or polymer mixture by irradiation with linearly polarised light. It is possible to vary the direction of orientation and the tilt angle within the polymer layer by controlling the direction of irradiation of the linearly polarised light. It will be appreciated that by selectively irradiating specific regions of the polymer layer it is possible to align very specific regions of the layer and provide layers with a defined angle of tilt. This orientation and tilt is retained in the polymer layer by the process of cross-linking.

It will be appreciated that the polymer layers of the present invention can also be used as orientation layers for liquid crystals and a preferred embodiment of the third aspect of the invention provides an orientation layer comprising one or more polymers according to the invention in a cross-linked form. Such orientation layers can be used in the manufacture of optical constructional elements, preferably in the production of hybrid layer elements.

The orientation layers are suitably prepared from a solution of the polymer material. The polymer solution is applied to a support optionally coated with an electrode (for example a glass plate coated with indium-tin oxide (ITO)) by a spin coating process, to produce homogeneous layers of 0.05 to 50 μm thickness. The resulting layer is imidised, if required, and may then be selectively orientated by irradiation with a high-pressure mercury vapour lamp, a xenon lamp or a pulsed UV laser, using a polariser and optionally a mask for creating images of structures. The irradiation time is dependent upon the output of the individual lamps and can vary from a few seconds to several hours. The cross-linking reaction can also be carried out by irradiation using filters that, for example, only allow the radiation suitable for the cross-linking reaction to pass through.

It will be appreciated that the polymer layers of the invention may be used in the production of optical or electro-optical devices having at least one orientation layer as well as unstructured and structured optical elements and multi-layer systems. A further embodiment of the third aspect of the invention provides an optical or electro-optical device comprising one or more polymers according to the first aspect of the invention in cross-linked form. The electro-optical devices may comprise more than one layers. The or each of the orientation layers may contain one or more regions of different spatial orientation.

The invention will now be described with reference to the following non-limiting examples in which Tg represents the glass temperature, C represents the crystalline phase, N represents the nematic phase, I represents the isotropic phase, pdi represents the polydispersity index and p represents the number of repeating units in the polymer. Relative molecular weights were determined by gel permeation chromatography (GPC) at 35° C. using THF as solvent with polystyrene added. Variations of these examples failing within the scope of the present invention will be apparent to a person skilled in the art.

EXAMPLES

Example 1

Preparation of Poly-[1-[11-[5-[4-[(E)-2-methoxycarbonylvinyl]benzoyloxy]-2-[6-[2-methoxy-(E)-4-(methoxycarbonylvinyl)phenoxy]oxyhexyl]benzoyloxy]undecyloxy-carbonyl]-1-methylethylene]

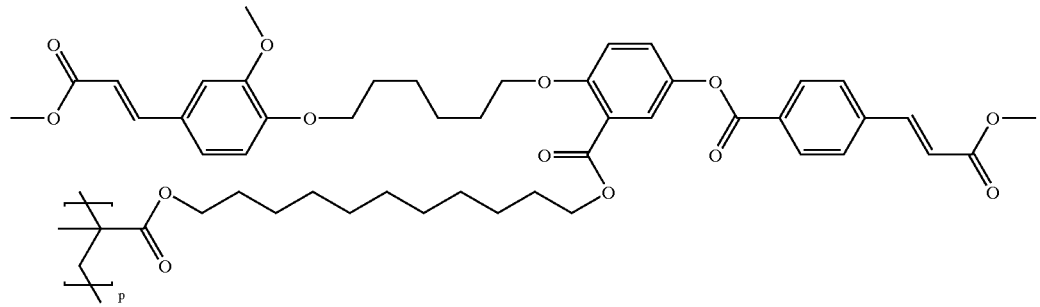

A mixture of 0.70 g (0.890 mmol) (E,E)-5-[4-(2-methoxycarbonylvinyl)benzoyloxy]-2-[6-[2-methoxy-4-(methoxycarbonylvinyl)phenoxy]oxyhexyl]benzoic acid 11-(2-methylacryloyloxy)undecyl ester and 1.32 mg (0.008 mmol) α,α'-azoisobutyronitrile (AIBN) in 4.0 ml dry tetrahydrofuran (THF) was degassed in a scalable tube. The tube was then sealed under argon and stirred at 60° C. for 17 h. The resulting polymer was diluted with 2.0 ml THF, precipitated into 350 ml diethyl ether and collected. The polymer was reprecipitated from THF (5.0 ml) into 400 ml methanol to yield 0.35 g, (52%)] Poly-[1-[11-[5-[4-[(E)-2-methoxycarbonylvinyl]benzoyloxy]-2-[6-[2-methoxy-(E)-4-(methoxycarbonylvinyl)phenoxy]oxyhexyl]benzoyloxy]undecyloxycarbonyl]-1-methylethylene as a solid; $M_n$=7.4× $10^4$, pdi=2.12, Tg=50.2° C., cl.p. (N/I) 68.1° C.

The (E,E)-5-[4-(2-methoxycarbonylvinyl)benzoyloxy]-2-[6-[2-methoxy-4-(methoxycarbonylvinyl)phenoxy]oxyhexyl]benzoic acid 11-(2-methylacryloyloxy)undecyl ester used as starting material was prepared in accordance with the following procedure:

Preparation of (E)-4-carboxylcinnamic acid methyl ester

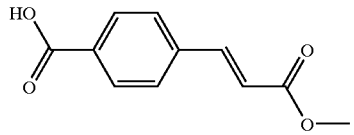

10.0 g (66.6 mmol) 4-carboxybenzaldehyde were dissolved in 100 ml toluene and 23.6 g (69.9 mmol) [(methoxycarbonyl)methyl]triphenylphosphorane were added. The reaction was slightly exothermic. The thick suspension was diluted with 50 ml toluene. After 18 h at room temperature the product was collected by filtration and was digest in 100 ml isopropyl alcohol at reflux temperature for 1 hour. The solid was then filtered off at 0° C., dried overnight at 45° C. under vacuum, resulting in 8.9 g (65%) (E)-4-carboxyl cinnamic acid methyl ester as white powder.

Preparation of 2-methlacrylic acid 11-bromoundecyl ester

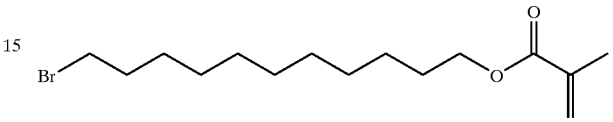

19.2 g (76.4 mmol) 11-bromo-1-undecanol, 7.2 g (84.1 mmol) methacrylic acid and 1.03 g (8.4 mmol) 4-dimethylaminopyridine were dissolved in 157 ml dichloromethane. The solution was subsequently cooled to 0° C. and then a solution of 17.4 g (84.2 mmol) dicyclohexylcarbodiimide in 80 ml dichloromethane was added dropwise at 0° C. over a period of 45 minutes. The reaction mixture was allowed to warm to room temperature, stirred for 19 hours and filtered. The filtrate was concentrated by evaporation. The residue was purified by chromatography using a silica gel column (170 g) and toluene as eluant to give 19.3 g (98.4%) 2-methylacrylic acid 11-bromoundecyl ester.

Preparation of 2,5-dihydroxybenzoic acid 11-(2-methylacryloyloxy)undecyl ester

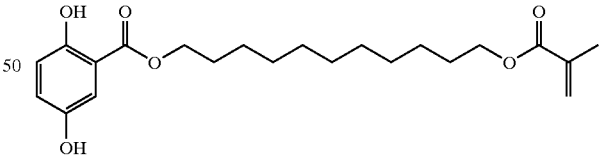

8.46 g (54.9 mmol) 2,5-dihydroxybenzoic acid was suspended in 55 ml acetonitrile. 8.24 ml (54.9 mmol) 1,8-diazabicyclo[5.4.0]undec-7-ene(1,5-5) (DBU) were added dropwise over a period of 10 minutes. The reaction temperature was allowed to rise to 40° C. The reaction mixture was cooled to room temperature and 19.3 g (60.4 mmol) 2-methacrylic acid 11-bromoundecyl ester was added and the resulting mixture was then reflux for 17.5 hours. The reaction mixture was cooled and then extracted using diethyl ether and water; the diethyl ether was washed firstly with water, then with 1N sulfuric acid and finally with water, dried over sodium sulfate, filtered and concentrated by rotary evaporation. The residue was recrystallised twice, firstly form a mixture of ethyl acetate (17 ml) and hexane (100 ml) and secondly form a mixture of tert-butyl methyl ether (50 ml) and hexane (100 ml) to give 17.1 g (79%) 2,5-dihydroxybenzoic acid 11-(2-methylacryloyloxy) ester as white crystals.

Preparation of (E)-2-Hydroxy-5-[4-(2-methoxycarbonylvinyl)benzoyloxy]benzoic acid 11-(2-methylacryloyloxy)undecyl ester

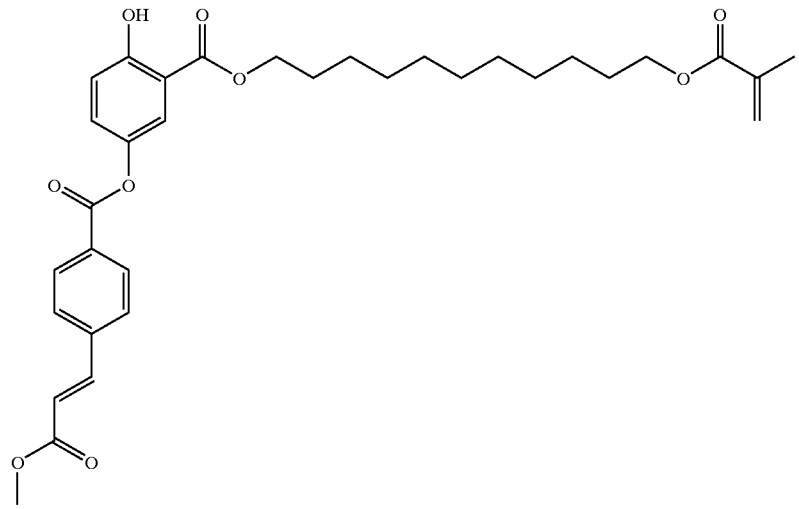

4,76 g (12.1 mmol) 2,5-dihydroxybenzoic acid 11-(2-methylacryloyloxy)ester, 2.50 g (12.1 mmol) (E)-4-carboxylcinnamic acid methyl ester and 0.37 g (3.0 mmol) 4-dimethylaminopyridine were dissolved in 30 ml of dichloromethane. A suspension of 2.32 g (12.1 mmol) N-(3-dimethylanopropyl)-N'-ethylcarbodiimide hydrochloride and 25 ml dichloromethane were added dropwise over a period of 1 hour. After 1.5 hour at room temperature the reaction mixture was extracted using dichloromethane and water, the dichloromethane was washed repeatedly with water, dried over sodium sulfate, filtered and concentrated by rotary evaporation. The residue was purified by chromatography using a silica gel column (240 g) using cyclohexane:ethyl acetate (9:1) as eluant to give 6.1 g (87%) (E)-2-hydroxy-5-[4-(2-methoxycarbonylvinyl)benzoyloxy]benzoic acid 11-(2-methylacryloyloxy)undecyl ester as white powder, m.p.=51° C.

Preparation of (E)-4-Hydroxy-3-methoxycinnamic acid methyl ester

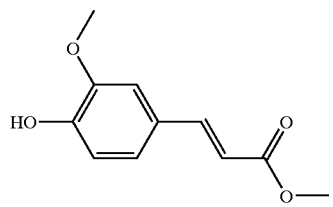

25 g (0.13 mmol) of (E)-4-hydroxy-3-methoxycinnamic acid was dissolved in 180 ml of methanol, and 5 ml of concentrated sulfuric acid was added thereto. The solution was heated at reflux for 2 hours. The majority of the methanol (about 150 ml) was removed by distillation and the remaining residue was poured into 500 ml of ice-water thereby to effect precipitation of the ester, which was then purified by suction filtration and washed firstly with cold water, then with a small amount of cold saturated sodium bicarbonate solution and finally with cold water and dried at 50° C. under a water-jet vacuum. The product was then purified by chromatography using silica gel (250 g) using dichloromethane:diethyl ether (19:1) as eluant to give 21.78 g of (E)-4-hydroxy-3-methoxycinnamic acid methyl ester in the form of a light-yellow oil.

Preparation of (E)-4-Hydroxyhexyloxy)-3-methoxycinnamic acid methyl ester

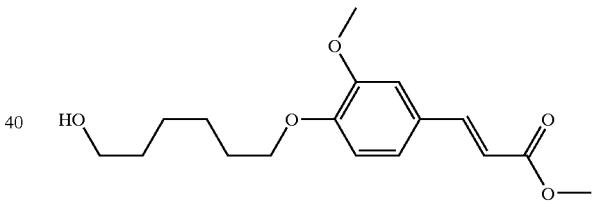

3.92 ml (25.2 mmol) of 1,6-hexanediol vinyl ether were added to a solution of 5.0 g (24.0 mmol) of (E)-4-hydroxy-3-methoxycinnamic acid methyl ester and 6.61 g (25.2 mmol) of triphenylphosphine in 150 ml of tetrahydrofuran. The colourless solution was subsequently cooled to 0° C. and then 11.5 ml (25.3 mmol) of a 40% solution of azodicarboxylic acid diethyl ester in toluene were added dropwise thereto over a period of 30 minutes. The mixture was subsequently allowed to react first for 30 minutes at 0° C. and then for 22.5 hours at room temperature. 150 ml of methanol and 10 drops of concentrated sulfuric acid were then added to the reaction solution and the mixture was stirred for 1.5 hours. The reaction mixture was then extracted using ethyl acetate and water. The ethyl acetate was washed with a saturated sodium bicarbonate solution and repeatedly with saturated sodium chloride solution, dried over magnesium sulfate, filtered and concentrated by evaporation. The resulting residue was purified by column chromatography using silica gel (470 g) using toluene:ethyl acetate (1:1) as eluant. Recrystallisation from ethyl acetate:hexane (3:5) gave 6.13 g of 4-(6-hydroxyhexyloxy)-3-methoxycinnamic acid methyl ester.

Preparation of (E,E)-5-[4-(2-Methoxycarbonylvinyl)benzoyloxy]-2-[6-[2-methoxy-4-(methoxycarbonylvinyl)phenoxy]oxyhexyl]benzoic acid 11-(2-methylacryloyloxy)undecyl ester

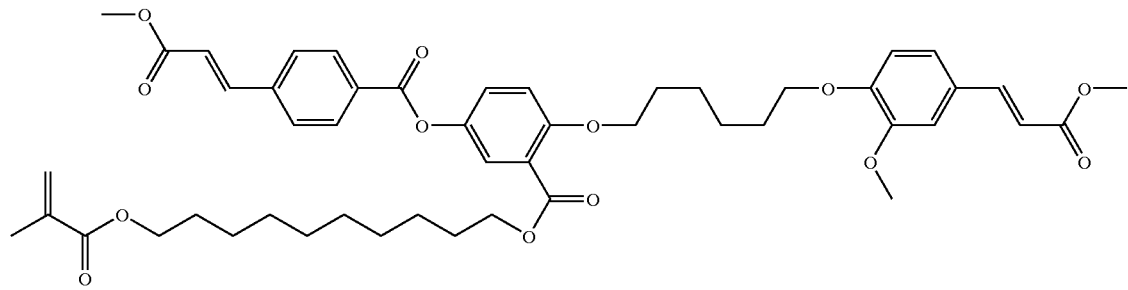

1.24 g (2.13 mmol) (E)-2-hydroxy-5-[4-(2-methoxycarbonylvinyl)benzoyloxy]benzoic acid 11-(2-methylacryloyloxy)undecyl ester, 0.66 g (2.13 mmol) 4-(6-hydroxyhexyloxy)-3-methoxycinnamic acid methyl ester and 0.59 g (2.24 mmol) of triphenylphosphine in 20 ml of tetrahydrofuran. The colourless solution was subsequently cooled to 0° C. and 0.98 ml (2.15 mmol) of a 40% solution of azodicarboxylic acid diethyl ester in toluene was added dropwise thereto over a period of 10 minutes. The mixture was subsequently allowed to react for 3 hours at 0° C. The reaction mixture was then partitioned between ethyl acetate and water, the organic phase was washed repeatedly with saturated sodium chloride solution, dried over magnesium sulfate, filtered and reduced in volume by evaporation. The resulting residue was added to a mixture of methanol and water (3:2). The resulting solid was separated from the solution by filtration and dried overnight at 45° C. under vacuum. The solid was purified by column chromatography using silica gel (150 g) and toluene:ethyl acetate (9:1) as eluant to give 1.40 g (75%) of (E,E)-5-[4-(2-methoxycarbonylvinyl)benzoyloxy]-2-[6-[2-methoxy-4-(methoxycarbonylvinyl)phenoxy]oxyhexyl]benzoic acid 11-(2-methylacryloyloxy)undecyl ester as white powder.

Example 2

Preparation of Poly-[1-[11-[(E,E)-2,5-di-[6-[2-methoxy-4-(methoxycarbonylvinyl)phenoxy]oxyhexyl]benzoyloxy]undecyloxycarbonyl]-1-methylethylene]

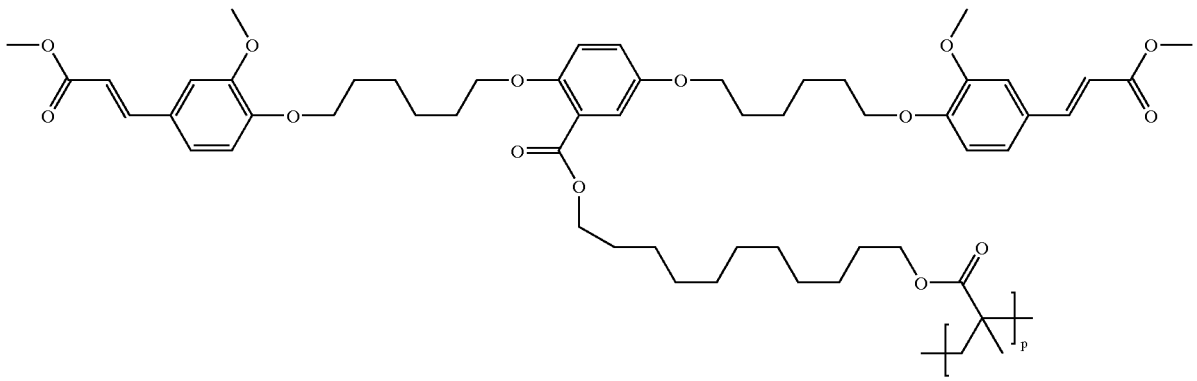

This was effected using the procedure according to Example 1 using 0.87 g (0.89 mmol) (E,E)-2,5-di-[6-[2-methoxy-4-(methoxycarbonylvinyl)phenoxy]oxyhexyl]benzoic acid 11-(2-methylacryloyloxy)undecyl ester to give 0.25 g (30%) poly-[1-[11-[(E,E)-2,5-di-[6-[2-methoxy-4-(methoxycarbonylvinyl)phenoxy]oxyhexyl]benzoyloxy]undecyloxycarbonyl]-1-methylethylene] as hard solid; $M_n = 6.9 \times 10^4$, pdi=1.95.

The (E,E)-2,5-di-[6-[2-methoxy-4-(methoxycarbonylvinyl)phenoxy]oxyhexyl]benzoic acid 11-(2-methylacryloyloxy)undecyl ester used as starting material was prepared in accordance with the following procedure:

Preparation of (E,E)-2,5-di-[6-[2-methoxy-4-(methoxycarbonylvinyl)phenoxy]oxyhexyl]benzoic acid 11-(2-methylacryloyloxy)undecyl ester

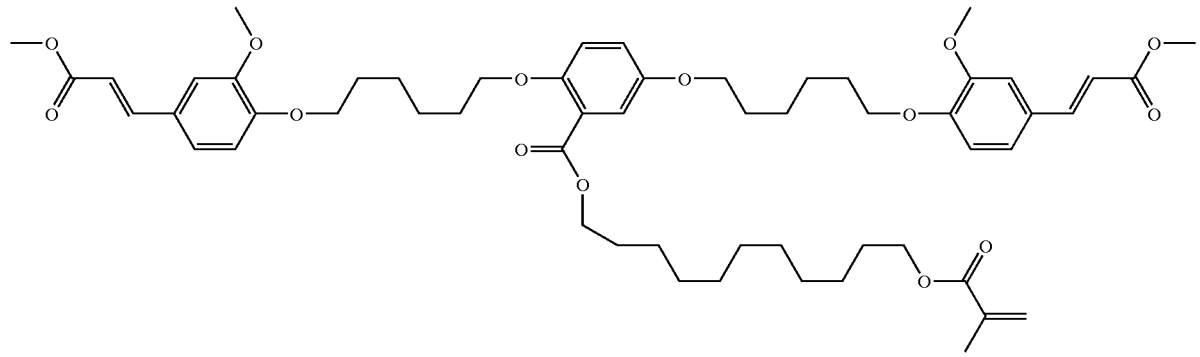

0.50 g (1.55 mmol) 2,5-dihydroxybenzoic acid 11-(2-methylacryloyloxy)ester, 0.96 g (3.10 mmol) (E)-4-(6-hydroxyhexyloxy)-3-methoxycinnamic acid methyl ester and 0.81 ml (3.26 mmol) of tributylphosphine were dissolved in 10 ml of tetrahydrofuran and 0.82 g (2.10 mmol) of 1,1'-(azodicarbonyl)dipiperidine were added. The mixture was allowed to react for 1 hour at room temperature. The reaction mixture was then extracted using ethyl acetate and water. The ethyl acetate was washed repeatedly with saturated sodium chloride solution, dried over magnesium sulfate, filtered and concentrated by evaporation. The resulting residue was purified by column chromatography using silica gel (150 g) using toluene:ethyl acetate (85:15) as eluant to give 0.82 g (59%) of (E,E)-2,5-di-[6-[2-methoxy-4-(methoxycarbonylvinyl)phenoxy]oxyhexyl]benzoic acid 11-(2-methylacryloyloxy)undecyl ester as white powder.

The following compounds were prepared in an analogous manner:

Poly-[1-[11-[(E,E)-3,5-di-[6-[2-methoxy-4-(methoxycarbonylvinyl)phenoxy]oxyhexyl]benzoyloxy]undecyloxycarbonyl]-1-methylethylene] Mn=1.07×10$^5$, pdi=2.90

Poly-[1-[11-[(E,E)-3,4-di-[6-[2-methoxy-4-(methoxycarbonylvinyl)phenoxy]oxyhexyl]benzoyloxy]undecyloxycarbonyl]-1-methylethylene] Mn=3.59×10$^5$, pdi=5.7

Example 3

Preparation of poly-[1-[11-[5-[6-[2-methoxy-4(E)-(methoxycarbonylvinyl)phenoxy]oxyhexyl]-2-[6-[3(E)-(3-methoxy-4-butoxyphenyl)acryloyloxy]oxyhexyl]benzoyloxy]undecyloxycarbonyl]-1-methylethylene]

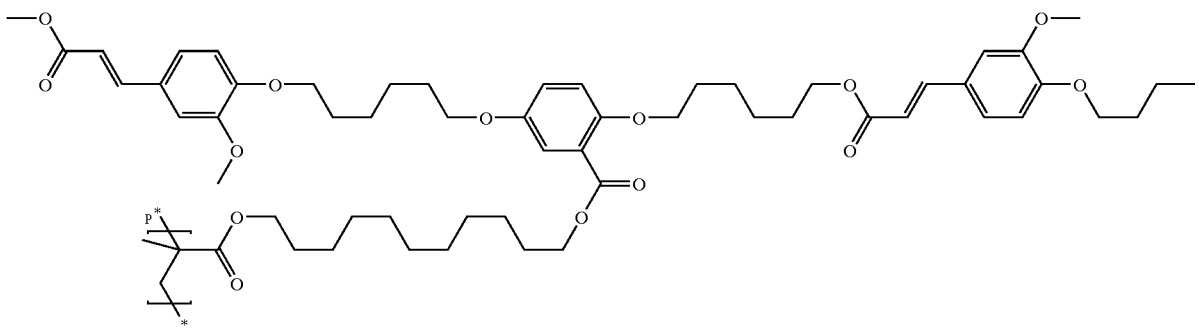

Following the procedure of Example 1 and using 0.634 g (0.624 mmol) (E,E)-5-[6-[2-methoxy-4-(methoxycarbonylvinyl)phenoxy]oxyhexyl]-2-[6-[3-(3-methoxy-4-butoxyphenyl)acryloyloxy]oxyhexyl]benzoic acid 11-(2-methylacryloyloxy)undecyl ester and 1.0 mg (0.0062 mmol) α,α'-azoisobutyronitrile (AIBN) yielded 0.464 g (73%) of Poly-[1-[11-[5-[6-[2-methoxy-4(E)-(methoxycarbonylvinyl)phenoxy]oxyhexyl]-2-[6-[3(E)-(3-methoxy-4-butoxyphenyl)acryloyloxy]oxyhexyl]benzoyloxy]undecyloxycarbonyl]-1-methylethylene] as a solid; $M_n=1.53\times10^5$, pdi=2.54, Tg=17.7° C.

The (E,E)-5-[6-[2-methoxy-4-(methoxycarbonylvinyl)phenoxy]oxyhexyl]-2-[6-[3-(3-methoxy-4-butoxyphenyl)acryloyloxy]oxyhexyl]benzoic acid 11-(2-methylacryloyloxy)undecyl ester used as starting material was prepared in accordance with the following procedure:

Preparations of (E)-4-butoxy-3-methoxycinnamic acid methyl ester

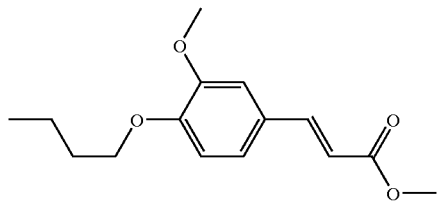

4.16 g (20.0 mmol) ferulic acid methyl ester was dissolved in 115 ml 2-butanone. 2.09 ml (22.0 mmol) n-butyl bromide and 11.06 g (80 mmol) potassium carbonate were added. The reaction suspension was then heated at reflux temperature for 20 hours. The reaction mixture was filtered. The filtrate was concentrated by evaporation. The crude product was recrystallised from 42 ml isopropyl alcohol yielded 4.85 g (92%) (4-butoxy-3-methoxycinnamic acid methyl ester as white crystals.

Preparation of (E)-4-butoxy-3-methoxycinnamic acid

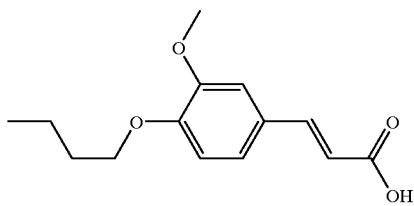

10 g (0.15 mmol) potassium hydroxide were dissolved in a mixture of 200 ml methyl alcohol and 5 ml water. 4.85 g (18.35 mmol) (E)-4-butoxy-3-methoxycinnamic acid methyl ester was added. The reaction mixture was subsequently heated to 60° C. After 2.5 h the mixture was concentrated by evaporation. The residue was dissolved in 100 ml cold water and acidified to pH=1 with 13.5 ml hydrochloric acid 37 wt. %. The product was filtered off, washed with water and dried at 50° C. under vacuum to give 4.24 g (92%) (E)-4-butoxy-3-methoxycinnamic acid as white crystals.

Preparation of (E)-4-butoxy-3-methoxycinnamic acid 6-hydroxyhexyl ester

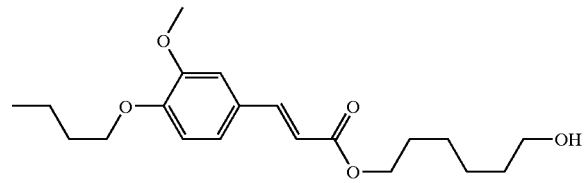

Following the procedure of Example 1 and using 1.38 g (5.50 mmol) (E)-4butoxy-3-methoxycinnamic acid, 0.84 g (5.50 mmol) 1,8-diazabicyclo[5.4.0]undec-7-ene(1,5-5) (DBU) and 0.68 g (5.0 mmol) 6-chlorohexanol gave 1.39 g (79%) (E)-4-butoxy-3-methoxycinnamic acid 6-hydroxyhexyl ester as colourless oil.

Preparation of (E)-2-Hydroxy-5-[6-[2-methoxy-4-(methoxycarbonylvinyl)phenoxy]oxyhexyl]benzoic acid 11-(2-methylacryloyloxy)undecyl ester

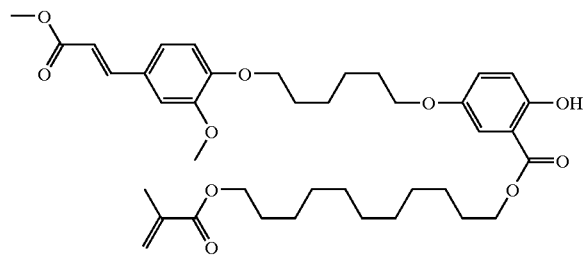

1.27 g (3.24 mmol) 2,5-dihydroxybenzoic acid 11-(2-methylacryloyloxy)ester, 1.0 g (3.24 mmol) 4-(6-hydroxyhexyloxy)-3-methoxycinnamic acid methyl ester and 0.89 g (3.40 mmol) of triphenylphosphine were dissolved in 20 ml of tetrahydrofuran. The colourless solution was subsequently cooled to 0° C. and then 1.48 ml (3.40 mmol) of a 40% solution of azodicarboxylic acid diethyl ester in toluene was added dropwise thereto over a period of 10 minutes. The mixture was subsequently allowed to react for 3 hours at 0° C. The reaction mixture was then partitioned between ethyl acetate and water, the organic phase was washed with repeatedly with saturated sodium chloride solution, dried over magnesium sulfate, filtered and concentrated by evaporation. The residue was digest in a mixture form methanol and water 3:2. The solid was then filtered off and dried overnight at 45° C. under vacuum. Chromatography of the solid on 150 g of silica gel using toluene:ethyl acetate 1:1 yielded 1.45 g (65%) of (E)-2-hydroxy-5-[6-[2-methoxy-4(methoxycarbonylvinyl)phenoxy]oxyhexyl]benzoic acid 11-(2-methylacryloyloxy)undecyl ester as colourless oil.

Preparation of (E,E)-5-[6-[2-methoxy-4-(methoxycarbonylvinyl)phenoxy]oxyhexyl]-2-[6-[3-(3-methoxy-4-butoxyphenyl)acryloyloxy]oxyhexyl] benzoic acid 11-(2-methylacryloyloxy)undecyl ester

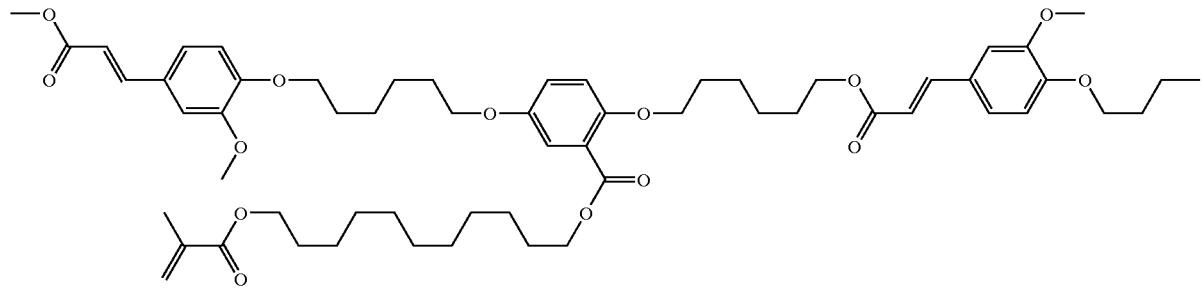

0.81 g (1.18 mmol) (E)-2-hydroxy-5-[6-[2-methoxy-4-(methoxycarbonylvinyl)phenoxy]oxyhexyl]benzoic acid 11-(2-methylacryloyloxy)undecyl ester, 0.414 g (1.18 mmol) 4-(6-hydroxyhexyloxy)-3-methoxycinnamic acid methyl ester and 0.31 ml (1.24 mmol) of tributylphosphine were dissolved in 10 ml of tetrahydrofuran to which a mixture of 0.313 g (1.24 mmol) of 1,1'-(azodicarbonyl) dipiperidine and 5 ml tetrahydrofuran was subsequently added in a dropwise fashion over a period of 1 hour. The mixture was allowed to react for 18 hours at room temperature. The reaction mixture was then partitioned between ethyl acetate and water, the organic phase was washed with repeatedly with saturated sodium chloride solution, dried over magnesium sulfate, filtered and concentrated by evaporation. Chromatography of the crude product on 120 g of silica gel using toluene:ethyl acetate 4:1 and crystallisation form tert-butyl methyl ether yielded 0.63 g (62%) (E,E)-5-[6-[2-methoxy-4-(methoxycarbonylvinyl)phenoxy] oxyhexyl]-2-[6-[3-(3-methoxy-4-butoxyphenyl) acryloyloxy]oxyhexyl]benzoic acid 11-(2-methylacryloyloxy)undecyl ester as white crystals.

Example 4

Preparation of Poly-[1-[11-[(E,E,E)-3,4,5-tri-[6-[2-methoxy-4-(methoxycarbonylvinyl)phenoxy] oxyhexyl]benzoyloxy]undecyloxycarbonyl]-1-methylethylene Preparation can be carried out analogously to Example 1 using 0.50 g (0.413 mmol) (E,E,E)-3,4,5-tri-[6-[2-methoxy-4-(methoxycarbonylvinyl)phenoxy]oxyhexyl]benzoic acid 11-(2-methylacryloyloxy)undecyl ester and (0.004 mmol) α,α'-azoisobutyronitrile (AIBN) yield Poly-[1-[11-[(E,E,E)-3,4,5-tri-[6-[2-methoxy-4-(methoxycarbonylvinyl) phenoxy]oxyhexyl]benzoyloxy]undecyloxycarbonyl]-1-methylethylene].

The (E,E,E)-3,4,5-tri-[6-[2-methoxy-4-(methoxycarbonylvinyl)phenoxy]oxyhexyl]benzoic acid 11-(2-methylacryloyloxy)undecyl ester used as starting material was prepared in accordance with the following procedure:

Preparation of 3,4,5-dihydroxybenzoic acid 6-(2-methacryloyloxy)hexyl ester

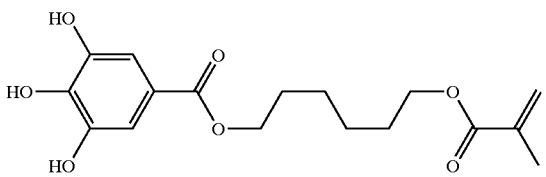

This was effected using the procedure according, to Example 1 using 6.08 g (32.3 mmol) gallic acid, 5.41 g (35.5 mmol) 1,8-diazabicyclo[5.4.0]undec-7-ene-(1,5-5) (DBU) and 6.38 g (21.5 mmol) 2-methacrylic acid 6-iodohexyl ester to give 2.43 g (33%)

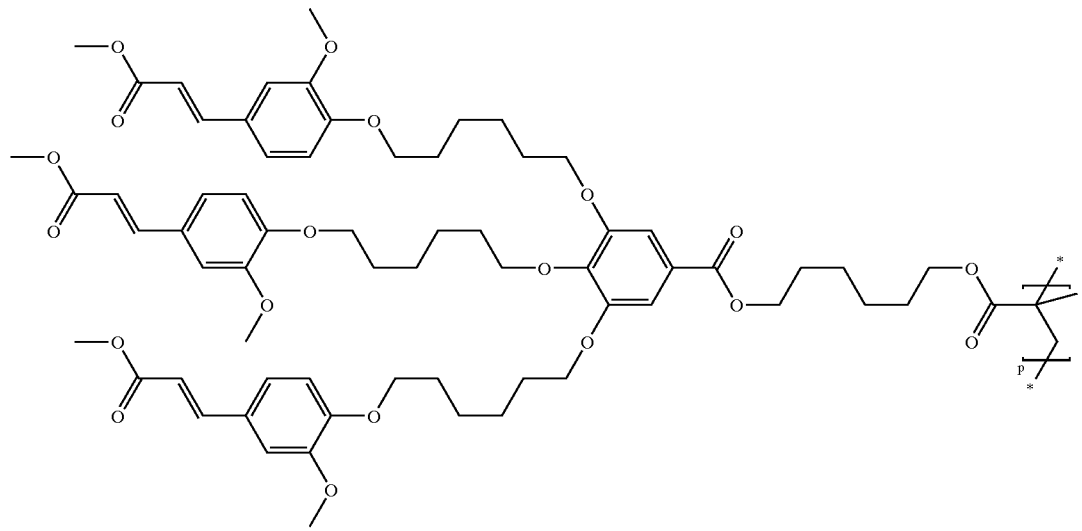

Preparation of (E,E,E)-3,4,5-tri-[6-[2-methoxy-4-(methoxycarbonylvinyl)phenoxy]oxyhexyl]benzoic acid 11-(2-methylacryloyloxy)undecyl ester

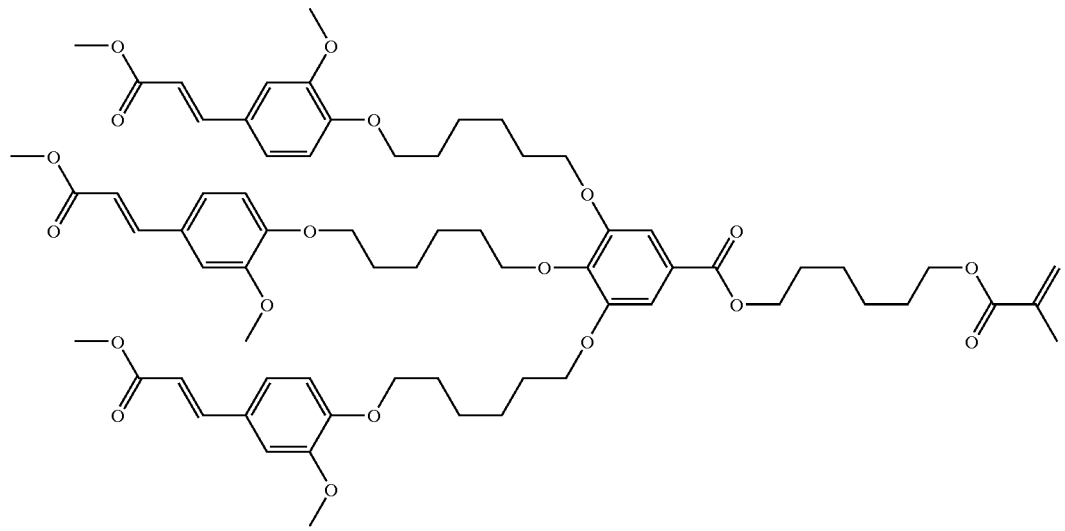

Following the procedure of Example 1 and using 1.00 g (2.95 mmol) 3,4,5-dihydroxybenzoic acid 6-(2-methacryloyloxy)hexyl ester, 2.32 g (8.87 mmol) triphenylphosphine, 2.73 g (8.87 mmol) (E)-4-(6-hydroxyhexyloxy)3-methoxycinnamic acid methyl ester and 4.03 ml (8.87 mmol) of a 40% solution of azodicarboxylic acid diethyl ester in toluene to give 0.95 g (27%) of (E,E,E)-3,4,5-tri-[6-[2-methoxy-4-(methoxycarbonylvinyl)phenoxy]oxyhexyl]benzoic acid 11-(2-methylacryloyloxy)undecyl ester as colourless oil.

Example 5

Polyimide 94.2 mg (0.4803 mmol) of 1,2,3,4-cyclobutantetracarboxylic acid dianhydride was added to a solution of 0.500 g (0.5336 mmol) of 3,5-diaminobenzoic acid 11-[2-[6-[2-methoxy-4-(methoxycarbonylvinyl)phenoxy]oxyhexyl]]-5-[4-(2-methoxycarbonylvinyl)benzoyloxy]benzoyloxy] undecyl ester in 3 ml of tetrahydrofuran. Stirring was then carried out at 0° C. for 2 hours. 10.4 mg (0.0530 mmol)) of 1,2,3,4-cyclobutantetracarboxylic acid dianhydride were added. The mixture was subsequently allowed to react for 69 hours at room temperature. The polymer mixture was diluted with 3.0 THF, precipitated into 150 ml diethyl ether and collected. The polymer was reprecipitated form THF (10 ml) into 500 ml water to yield, after drying at room temperature under vacuum, polyamic acid.

The 3,5-diaminobenzoic acid 11-[2-[6-[2-methoxy-4-(methoxycarbonylvinyl)phenoxy]oxyhexyl]]-5-[4-(2-methoxycarbonyl-vinyl)benzoyloxy]benzoyloxy]undecyl ester used as starting material was prepared in accordance with the following procedure:

3,5-Dinitrobenzoic acid 11-bromoundecyl ester

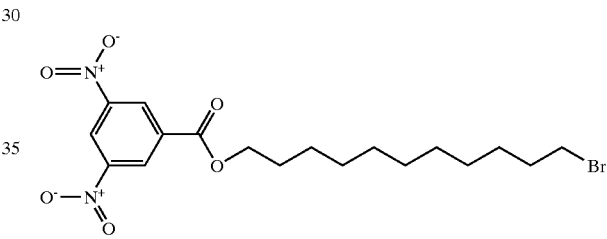

11.4 g (45.4 mmol) 11-bromo-1-undecanol, 11.0 g (47.7 mmol) 3,5-dinitrobenzoyl chloride and 54 mg 4-dimethylaminopyridine were dissolved in 94 ml dichloromethane. The solution was subsequently cooled to 0° C. and then 18.3 ml is (227 mmol) pyridine was added dropwise, in the course of 25 minutes. After 4.5 hours at 0° C. the reaction mixture was partitioned between dichloromethane and water. The organic phase was washed repeatedly with water, dried over sodium sulfate, filtered and concentrated by rotary evaporation. Chromatography of the residue on 200 g silica gel using toluene yielded 18.1 g (90%) 3,5-dinitrobenzoic acid 11-bromoundecyl ester as yellow powder.

3,5-Dinitrobenzoic acid 11-[2,5-dihydroxybenzoyloxy] undecyl ester

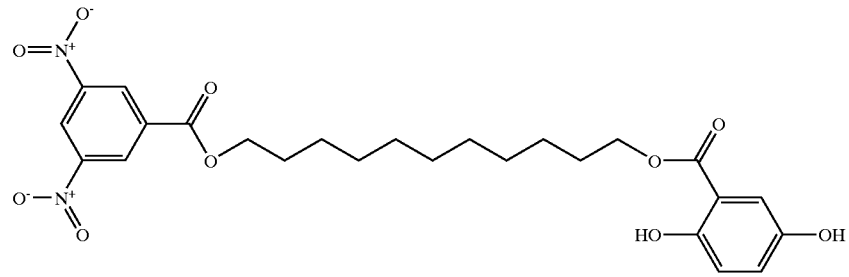

2.78 g (18.0 mmol) 2,5-dihydroxybenzoic acid was dissolved in 36 ml dimethylformamide. 2.96 ml (19.8 mmol) 1,8-diazabicyclo[5.4.0]undec-7-ene(1,5-5) (DBU) was added dropwise in the course of 15 minutes. The reaction temperature rose to 30° C. and 8.83 g (19.8 mmol) 3,5-dinitrobenzoic acid 11-bromoundecyl ester was subsequently added in one portion. The mixture was then heated at 80° C. for 2 hours. The reaction mixture was cooled and then partitioned between dichloromethane and 1N hydrochloric acid; the organic phase was washed twice with water, dried over sodium sulfate, filtered and concentrated by rotary evaporation. Chromatography of the residue on 200 g silica gel using Toluene yielded 5.28 g (57%) 3,5-dinitrobenzoic acid 11-[2,5-dihydroxybenzoyloxy]undecyl ester as yellow powder.

3,5-Dinitrobenzoic acid 11-[2-hydroxy-5-[4-(2-methoxycarbonylvinyl)benzoyloxy]benzoyloxy]undecyl ester 4-carboxyl cinnamic acid methyl ester and 0.15 g (1.20 mmol) 4-dimethylaminopyridine were dissolved in 12 ml of dichloromethane. A suspension of 0.92 g (4.82 mmol) N-(3-dimethylaminopropyl)-N'-ethylcarbodiimide hydrochloride and 10 ml dichloromethane were added dropwise in the course of 45 minutes. After 3 hours at room temperature the reaction mixture was partitioned between dichloromethane and water; the organic phase was washed repeatedly with water, dried over sodium sulfate, filtered and concentrated by rotary evaporation. Chromatography of the residue on 100 g silica gel using toluene yielded 2.63 g (77%) 3,5-dinitrobenzoic acid 11-[2-hydroxy 5-[4-(2-methoxycarbonyl-vinyl)benzoyloxy]benzoyloxy]undecyl ester as yellow powder.

3,5-Dinitrobenzoic acid 11-[2-[6-[2-methoxy4-(methoxycarbonylvinyl)phenoxy]oxyhexyl]-5-[4-(2-

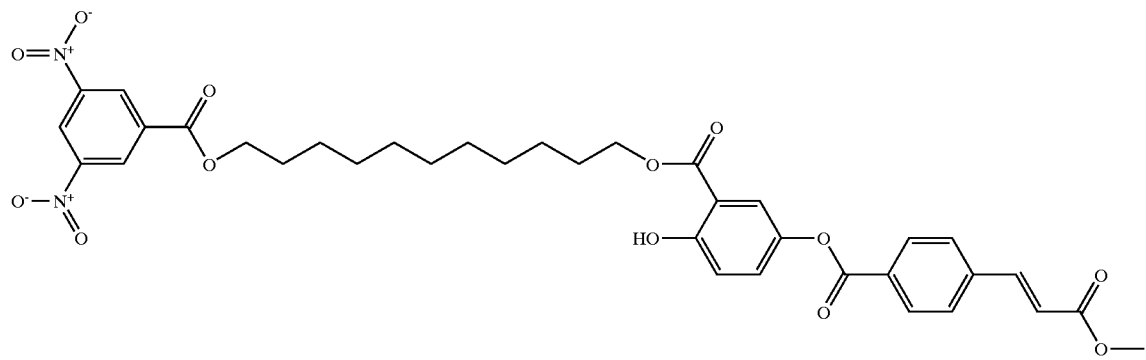

2.50 g (4.82 mmol) 3,5-Dinitrobenzoic acid 11-[2,5-dihydroxybenoyloxy]undecyl ester, 0.99 g (4.82 mmol) (E)- methoxycarbonylvinyl)benzoyloxy]benzoloxy]undecyl ester

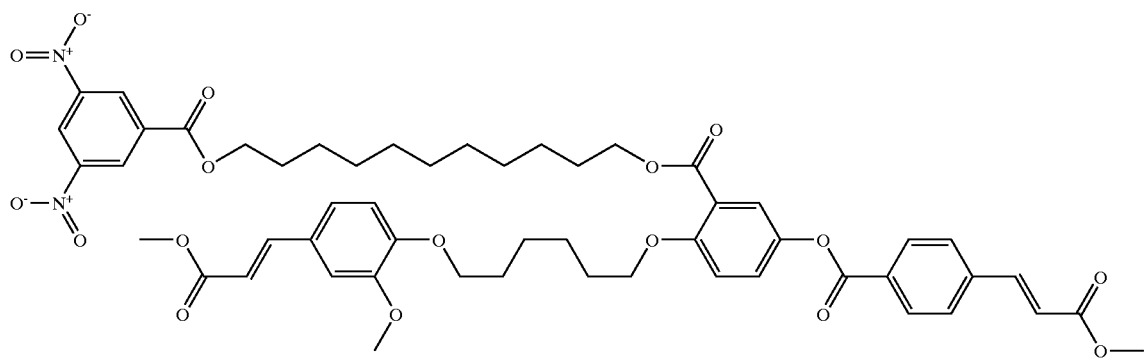

1.00 g (1.41 mmol) 3,5-dinitrobenzoic acid 11-[2-hydroxy-5-[4-(2-methoxycarbonylvinyl)benzoyloxy]benzoyloxy]undecyl ester, 0.436 g (1.41 mmol) (E)-4-(6-hydroxyhexyloxy)-3-methoxycinnamic acid methyl ester and 0.37 ml (1.48 mmol) of tributylphosphine were dissolved in 10 ml of tetrahydrofuran and 0.37 g (1.48 mmol) of 1,1'-(azodicarbonyl)dipiperidine is added. The mixture was allowed to react for 1 hour at room temperature. The reaction mixture was then partitioned between ethyl acetate and water, the organic phase was washed with repeatedly with saturated sodium chloride solution, dried over magnesium sulfate, filtered and concentrated by evaporation. Chromatography of the solid on of silica gel yield 3,5-Dinitrobenzoic acid 11-[2-[6-[2-methoxy-4-(methoxycarbonylvinyl)phenoxy]oxyhexyl]-5-[4-(2-methoxycarbonylvinyl)benzoyloxy]benzoyloxy]undecyl ester.

3,5-Diaminobenzoic acid 11-[2-[6-[2-methoxy-4-(methoxycarbonylvinyl)phenoxy]oxyhexyl]-5-[4-(2-methoxycarbonylvinyl)benzoyloxy]benzoyloxy]undecyl ester

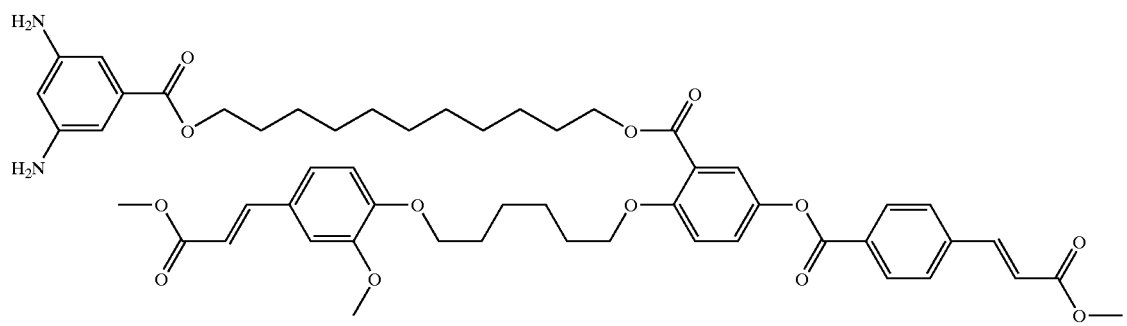

0.997 g (1.00 mmol) 3,5-Dinitrobenzoic acid 11-[2-[6-[2-methoxy-4-(methoxycarbonylvinyl)phenoxy]oxyhexyl]-5-[4-(2-methoxycarbonylvinyl)benzoyloxy]benzoyloxy]undecyl ester and 0 g (4.00 mmol) of ammonium chloride were suspended in 15 ml of a mixture consisting of methanol:water 9:1. 1.31 g (20.0 mmol) of zinc was then added in one portions. After 0.5 hour at room temperature 20 ml of a mixture consisting of methanol:water 9:1 is added to the thick suspension. After a further 21 hours the reaction suspension was partitioned between dichloromethane and water. The resulting suspension was filtered, the organic phase was washed with a saturated sodium bicarbonate solution and repeatedly with water. The organic phase was then dried over sodium sulfate, filtered and concentrated by evaporation. Chromatography of the residue on silica yield 3,5-Diaminobenzoic acid 11-[2-[6-[2-methoxy-4-(methoxycarbonylvinyl)phenoxy]oxyhexyl]-5-[4-(2-methoxycarbonylvinyl)benzoyloxy]benzoyloxy]undecyl ester.

Example 6

Preparation of Poly-[1-[6-[3,5-bis[[2-methoxy-4-[(E)-2-(methoxycarbonyl)vinyl]phenoxy]methyl]hexyloxycarbonyl]-1-methyl-ethylene]

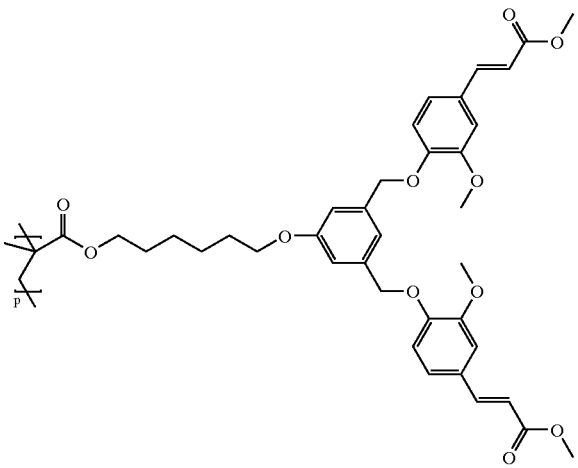

A solution of 0.46 g (0.63 mmol) 2-methylacrylic acid 6-[3,5-bis[[2-methoxy-4-[(E)-2-(methoxycarbonyl)vinyl]phenoxy]methyl]phenoxy]hexyl ester and 1.0 mg (0.0063 mmol) α.α'-azoisobutyronitrile (AIBN) in 1.6 ml dry tetrahydrofuran (THF) was degassed in a Schlenk tube and sealed under argon. The mixture was stirred at 55° C. for 15 h. The resulting polymer was precipitated into 500 ml methanol and collected. The polymer was reprecipitated from 3.0 ml THF into 500 ml diethylether at 0° C. to yield 0.2 g (46%) Poly-[1-[6-[3,5-bis[[2-methoxy-4-[(E)-2-(methoxycarbonyl)vinyl]phenoxy]methyl]-phenoxy]hexyloxycarbonyl-1-methyl-ethylene] as a white solid.

The 2-methylacrylic acid 6-[3,5-bis[[2-methoxy-4-[(E)-2-(methoxycarbonyl)vinyl]phenoxy]methyl]phenoxy]hexyl ester used as starting material was prepared in accordance with the following procedure:

Preparation of 5-[(6-Chlorohexyl)oxy]isophthalic acid dimethyl ester

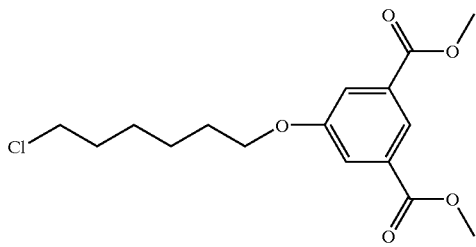

13.02 g (95.3 mmol) of 6-chlorohexanol were added to a solution of 20.04 g (95.3 mmol) of 5-hydroxyisophthalic acid dimethyl ester and 47.4 g (180.5 mmol) of triphenylphosphine in 300 ml of tetrahydrofuran. The colourless solution was cooled to 0° C. and then 79 ml (180.5 mmol) of a 40% solution of azodicarboxylic acid diethyl ester in toluene were added dropwise over a period of 2 hours and 45 minutes. The mixture was allowed to react for another 30 minutes at 0° C. and then for 22 hours at room temperature. The reaction mixture was concentrated by evaporation under vacuum. The residue was filtered through silica gel using dichloromethane:diethylether (85:15) as eluent. The filtrate was concentrated in vacuum and further purified by column chromatography on silica gel with hexane:ethyl acetate (9:1) to give 17.12 g (55%) of 5-[(6-chlorohexyl)oxy]isophthalic acid dimethyl ester as a white solid.

Preparation of [3-[(6-chlorohexyl)oxy]-5-[hydroxymethyl]phenyl]methanol

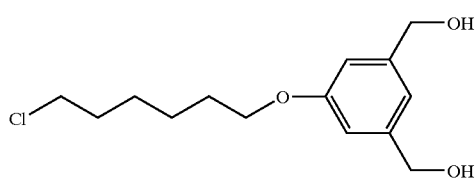

6.5 g (19.8 mmol) 5-[(6-chlorohexyl)oxy]isophthalic acid dimethyl ester were dissolved in 65 ml tetrahydrofuran in an atmosphere of argon. The colourless solution was cooled to −25° C. and then 42 ml (41.6 mmol) of a 1 molar solution of lithiumaluminiumhydrid in tetrahydrofuran were added dropwise over a period of 30 minutes. The reaction mixture was carefully quenched in sequence first with 5 ml of methanol and then with 50 ml of a 1 molar solution of HCl in water. The suspension was stirred for 1 hour at room temperature and subsequently filtered through speedex. The solid residue was washed carefully with 100 ml of tert.-butyl-methylether. The organic phase of the filtrate was separated, washed with 100 ml of a saturated sodium bicarbonate solution and 100 ml of water, dried over magnesium sulfate, filtered and concentrated in vacuum. Column chromatography of the crude product on 250 g of silica gel using dichloromethane:methanol (9:1) as eluent gave 5 g (93%) of [3-[(6-chlorohexyl)oxy]-5-[hydroxymethyl]phenyl]methanol as a white solid.

Preparation of (E)-3-[4-[[3-[(6-Chorohexyl)oxy]-5-[[2-methoxy-4-[(E)-2-(methoxycarbonyl)vinyl]phenoxy]methyl]benzyl]oxy]-3-methoxyphenyl]acrylic acid methyl ester

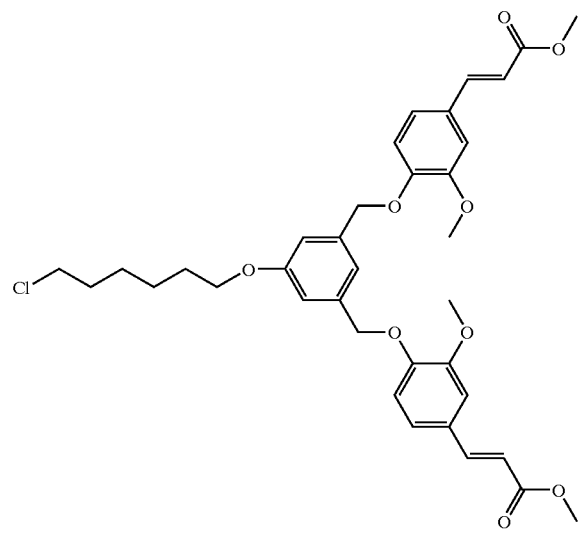

1.5 g (5.5 mmol) [3-[(6-chlorohexyl)oxy]-5-[hydroxymethyl]phenyl]methano] were added to a solution of 2.86 g (13.7 mmol) (E)-4-hydroxy-3-methoxycinnamic acid methyl ester (see Example 1) and 3.61 g (13.7 mmol) triphenylphosphine in 20 ml tetrahydrofuran. The colourless solution was cooled to 0° C. and then 6 g (13.7 mmol) of a 40% solution of azodicarboxylic acid diethyl ester in toluene were added dropwise over a period of 2 hours. The mixture was allowed to react for 2 hours at 0° C. and then for 22 hours at room temperature. The reaction mixture was concentrated in vacuum. The solid residue was dissolved in 50 ml of dichloromethane, washed with 30 ml of an 1 M HCl solution, 50 ml of a saturated sodium bicarbonate solution and repeatedly with water, dried over magnesium sulfite, filtered and concentrated by vacuum evaporation. The semi-crystalline residue was dissolved in 15 ml methanol at 60° C. The final product crystalized on standing at −20° C. overnight. Recrystallization from 38 ml of methanol gave 3.5 g (96%) of (E)-3-[4-[[3-[(6-chlorohexyl)oxy]-5-[[2-methoxy-4-[(E)-2-(methoxycarbonyl)vinyl]phenoxy]methyl]benzyl]oxy]-3-methoxyphenyl]acrylic acid methyl ester as white crystals.

Preparation of 2-Methylacrylic acid 6-[3,5-bis[[2-methoxy-4-[(E)-2-(methoxycarbonyl)vinyl]phenoxy]methyl]phenoxy]hexyl ester

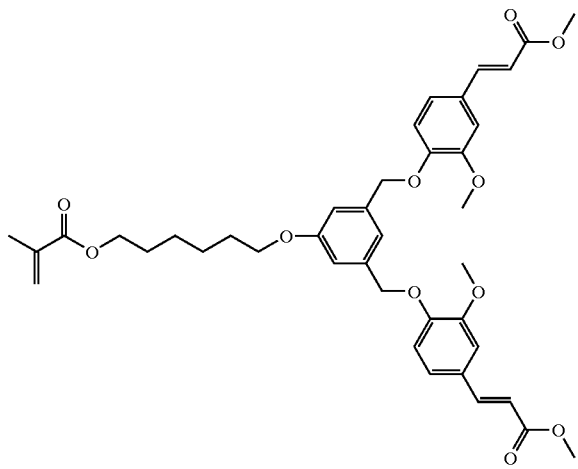

382 mg (2.5 mmol) 1,8-diazabicyclo[5.4.0]undec-7-ene (1,5-5) (DBU) in 4 ml N,N-dimethylformamide were added dropwise to a solution of 200 mg (2.3 mmol) 2-methylacrylic acid in 8 ml N,N-dimethylformamide over a period of 35 minutes. After addition of 4 mg phenothiazine, 1.5 g (2.3 mmol) (E)-3-[4-[[3-[(6-chlorohexyl)oxy]-5-[[2-methoxy-4-[(E)-2-(methoxycarbonyl)vinyl]phenoxy]methyl]benzyl]oxy]-3-methoxyphenyl]acrylic acid methyl ester and 84 mg tetrabutylammonium iodide the resulting mixture was stirred at 80° C. for 25 hours. The reaction mixture was poured into 50 ml of an ice cold 1 M HCl solution. The aqueous phase was extracted three times with 50 ml ethyl acetate. The organic phase was washed with 50 ml of a saturated sodium bicarbonate solution and repeatedly with water, dried over magnesium sulfate, filtered and concentrated by vacuum evaporation. Purification of the residue by column chromatography on 275 g silica gel using hexane: ethyl acetate (1:1) as eluent yielded 1.46 g (90%) of 2-methylacrylic acid 6-[3,5-bis[[2-methoxy-4-[(E)-2-(methoxycarbonyl)vinyl]phenoxy]methyl]phenoxy]hexyl ester as a yellowish oil.

Example 7

Preparation of Poly-[1-[6-[3,5-bis[[2-methoxy-4-[(E)-2-(methoxycarbonyl)vinyl]phenoxy]methyl]phenoxy]hexyloxycarbonyl]-1-methyl-ethylene-co-1-[2-[4-[(E)-2-(methoxycarbonyl)vinyl]phenoxy]ethoxycarbonyl]-1-methyl-ethylene] (1:1)

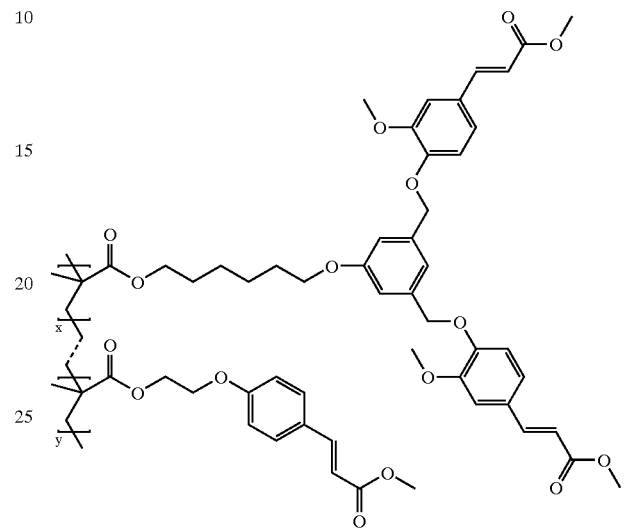

A solution of 0.50 g (0.71 mmol) 2-methylacrylic acid 6-[3,5-bis[[2-methoxy-4-[(E)-2-(methoxycarbonyl)vinyl]phenoxy]methyl]phenoxy]hexyl ester, 0.21 g (0.71 mmol) 2-methylacrylic acid 2-[4-[(E)-2-(methoxycarbonyl)vinyl]phenoxy]ethyl ester and 2.3 mg (0.014 mmol) α.α'-azoisobutyronitrile (AIBN) in 2.8 ml dry tetrahydrofuran (THF) was degassed in a Schlenk tube and sealed under argon. The mixture was stirred at 55° C. for 21 h. The resulting polymer was precipitated into 700 ml diethylether and collected. The polymer was reprecipitated from 5 ml THF into 500 ml diethylether to yield 0.58 g (82%) Poly-[1-[6-[3,5-bis[[2-methoxy-4-[(E)-2-(methoxycarbonyl)vinyl]phenoxy]methyl]phenoxy]hexyloxycarbonyl]-1-methyl-ethylene-co-1-[2-[4-[(E)-2-(methoxycarbonyl)vinyl]phenoxy]ethoxycarbonyl]-1-methyl-ethylene] (1:1) as a white solid The 2-methylacrylic acid 2-[4[(E)-2-(methoxycarbonyl)vinyl]phenoxy]ethyl ester used as comonomer was prepared according to the following procedure:

Preparation of 3-(4-Hydroxyphenyl)acrylic acid methyl ester

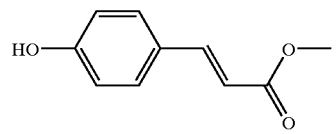

51.2 g (312 mmol) of p-coumaric acid were dissolved in 330 ml of methanol and treated with 10 ml of concentrated sulphuric acid. The solution was heated under reflux for 2 hours. Subsequently the majority of the methanol (about 200 ml) was distilled off and the residue remaining behind was poured into 1.3 l of ice-water. The separated ester was filtered off under suction and washed in succession with cold water, with a small amount of cold NaHCO$_3$ solution and again with cold water. Drying at 50° C. in a water-jet vacuum gave 51.1 g of 3-(4-hydroxyphenyl)acrylic acid methyl ester in the form of a light brownish coloured powder.

Preparation of (E)-3-[4-[2-Hydroxyethoxy]phenyl] acrylic acid methyl ester

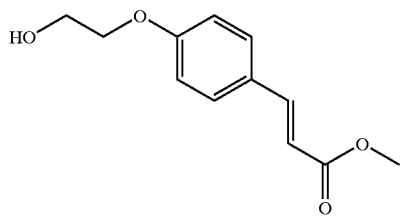

30 g (168 mmol) of 3-(4-hydroxyphenyl)acrylic acid methyl ester, 29 g (210 mmol) of anhydrous K$_2$CO$_3$ and a spatula tip of KI were placed in 200 ml of dimethylformamide. 14.91 g (185 mmol) of 2-chloroethanol were added dropwise at 85° C. within 5 minutes while stirring. The batch was stirred at 85° C. for a further 3 days. Subsequently, the salts were filtered off and the filtrate was concentrated to dryness in a water-jet vacuum. 16.1 g of (E)-3-[4-[2-hydroxyethoxy]phenyl]acrylic acid methyl ester were obtained in the form of white crystals after recrystallization from i-propanol.

Preparation of 2-Methylacrylic acid 2-[4-[(E)-2-(methoxycarbonyl)vinyl]phenoxy]-ethyl ester

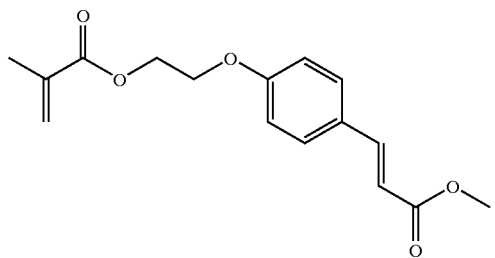

2.56 g (30 mmol) of methacrylic acid in 10 ml of THF were slowly added dropwise to a solution of 6 g (27 mmol) of (E)-3-[4-[2-hydroxyethoxy]phenyl]acrylic acid methyl ester, 5.85 g (28.3 mmol) of N,N'-dicyclohexylcarbodiimide (DCC) and 0.37 g (3 mmol) of 4-dimethylamino-pyridine in 80 ml of tetrahydrofuran (THF). The batch was stirred at room temperature overnight. In order to complete the reaction there were added firstly a further 1.46 g (7.1 mmol) of DCC and, after stirring for one hour, a further 0.5 g (5.9 mmol) of methacrylic acid. The batch was stirred for a further 24 hours, filtered and the filtrate was extracted 3 times each time with 200 ml of 5% acetic acid and 200 ml of water. The ether phase was dried over Na$_2$SO$_4$, evaporated and the residue was recrystallized from cyclohexane. Subsequently, the still slightly impure product was filtered over a thin silica gel layer (eluent:diethyl ether/hexane=1:1). This gave 8.3 g of 2-methylacrylic acid 2-[4-[(E)-2-(methoxycarbonyl)vinyl]phenoxy]ethyl ester as a white powder with a melting point of 81–82° C. and an absorption maximum of $\lambda_{max.}$ (in CH$_2$Cl$_2$)=306.5 nm ($\epsilon$=23675 l/mmol cm).

Example 8

Preparation of Poly-[1-[6-[3-[2-methoxy-4-[2-cyano-(E)-2-(methyoxycarbonyl)vinyl]
phenoxymethyl]-5-[2-methoxy-4-[(E)-2-(methoxycarbonyl)vinyl]phenoxymethyl]phenoxy]
hexyloxycarbony]-1-methyl-ethylene]

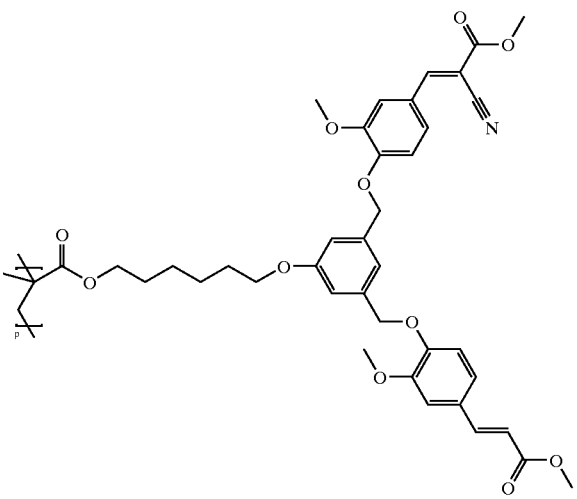

A solution of 0.35 g (0.48 mmol) 2-methylacrylic acid 6-[3-[2-methoxy-4-[2-cyano-(E)-2-(methoxycarbonyl) vinyl]phenoxymethyl]-5-[2-methoxy-4-[(E)-2-methoxycarbonyl)vinyl]phenoxymethyl]phenoxy]hexyl ester and 0.78 mg (0.0048 mmol) α,α'-azoisobutyronitrile (AIBN) in 1.2 ml dry tetrahydrofuran (THF) was degassed in a Schlenk tube and sealed under argon. The mixture was stirred at 55° C. for 16.5 h. The resulting polymer was precipitated into 350 ml methanol and collected. The polymer was reprecipitated from 3 ml THF into 350 ml methanol to yield 0.11 g (31%) Poly-[1-[6-[3-[2-methoxy-4-[2-cyano-(E)-2-(methoxycarbonyl)vinyl]phenoxymethyl]-5-[2-methoxy-4-[(E)-2-(methoxycarbonyl)vinyl] phenoxymethyl]phenoxy]hexyloxycarbonyl]-1-methylethylene] as a yellow solid.

The 2-methylacrylic acid 6-[3-[2-methoxy-4-[2-cyano-(E)-2-(methoxycarbonyl)vinyl]phenoxymethyl]-5-[2-methoxy-4-[(E)-2-(methoxycarbonyl)vinyl] phenoxymethyl]phenoxy]hexyl ester used as starting material was prepared in accordance with the following procedure:

Preparation of (E)-3-[4-[3-[(6-Chlorohexyl)oxy]-5-[hydroxymethyl]benzyloxy]-3-methoxyphenyl] acrylic acid methyl ester

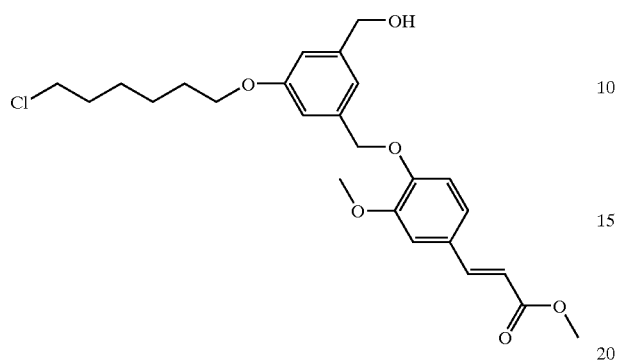

2.7 g (10 mmol) [3-[(6-chlorohexyl)oxy]-5-[hydroxymethyl]phenyl] methanol (Example 6) were added to a solution of 2.6 g (12.5 mmol) (E)-4-hydroxy-3-methoxycinnamic acid methyl ester (Example 1) and 3.38 g (12.5 mmol) triphenylphosphine in 40 ml tetrahydrofuran. The colourless solution was cooled to 0° C. and then 5.2 ml (12.5 mmol) of a 40% solution of azodicarboxylic acid diethyl ester in toluene were added dropwise over a period of 2 hours. The mixture was allowed to react for 2 hours at 0° C. and then for 15 hours at room temperature. The reaction mixture was poured into an ice cold 1 M solution of HCl. The aqueous phase was extracted three times with a mixture of tert-butyl-methylether/ethyl acetate. The organic phase was washed with a saturated sodium bicarbonate solution and repeatedly with water, dried over magnesium sulfate, filtered and concentrated in vacuum. Purification of the residue by column chromatography on silica gel using hexane:ethyl acetate (1:1) as eluent yielded 2.2 g (48%) of (E)-3-[4-[3-[(6-chlorohexyl)oxy]-5-[hydroxymethyl]benzyloxy]-3-methoxyphenyl]acrylic acid methyl ester as an oily product that solidified on standing.

Preparation of 2-Cyano-(E)-3-(4-hydroxy-3-methoxyphenyl)acrylic acid methyl ester

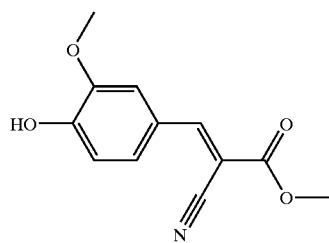

0.2 ml of piperidine were added carefully to a solution of 4.6 g (30 mmol) of vanillin, 3.4 ml (30.3 mmol) of cyanoacetic acid methyl ester and 0.5 ml of ethanol held at 45° C. The product started to precipitate on cooling to room temperature. The cold reaction mixture was diluted with 8 ml of ethanol, filtered and washed with cold ethanol to give 6.5 g (93%) of 2-cyano-(E)-3-(4-hydroxy-3-methoxyphenyl)acrylic acid methyl ester in form of yellow crystals.

Preparation of (E)-3-[4-[[3-[(6-chlorohexyl)oxy]-5-[[2-methoxy-4-[(E)-2-(methoxycarbonyl)vinyl] phenoxy]methyl]benzyl]oxy]-3-methoxyphenyl]-2-cyanoacrylic acid methyl ester

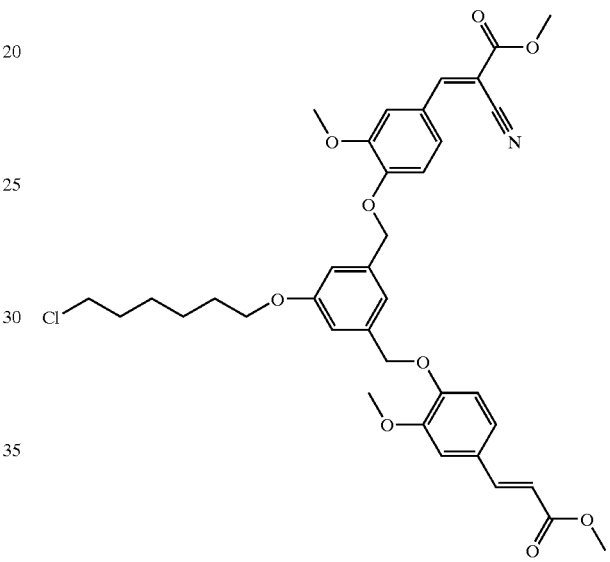

1 g (2.2 mmol) (E)-3-[4-[3-[(6-chlorohexyl)oxy]-5-[hydroxymethyl]benzyloxy]-3-methoxyphenyl]acrylic acid methyl ester was added to a solution of 0.62 g (2.7 mmol) 2-cyano-(E)-3-(4-hydroxy-3-methoxyphenyl)acrylic acid methyl ester and 0.73 g (2.7 mmol) triphenylphosphine in 10 ml tetrahydrofuran. The solution was cooled to 0°C. and then 1.1 ml (2.7 mmol) of a solution of azodicarboxlic acid diethyl ester in toluene were added dropwise. The mixture was allowed to react for 1 hour at 0° C. and then it was poured into an ice cold 1 M solution of HCl. The mixture was extracted three times with tert.-butyl-methylether/ethyl acetate. The organic phase was washed with a saturated sodium bicarbonate solution and repeatedly with water, dried over magnesium sulfates filtered and concentrated in vacuum. The solid residue was first treated with diethylether, filtered and then it was recrystallized twice from tert.-butyl-methylether to give 1.1 g (79%) of (E)-3-[4-[[3-[(6-Chlorohexyl)oxy]-5-[[2-methoxy-4-[(E)-2-(methoxycarbonyl)vinyl]phenoxy]methyl]benzyl]oxy)-3-methoxyphenyl]-2-cyanoacrylic acid methyl ester in form of slightly yellow crystals.

Preparation of 2-Methylacrylic acid 6-[3-[2-methoxy-4-[2-cyano-(E)-2-(methoxycarbonyl]vinyl] phenoxymethyl]-5-[2-methoxy-4-[(E)-2-(methoxy-carbonyl)vinyl]phenoxymethyl]phenoxy]hexyl ester

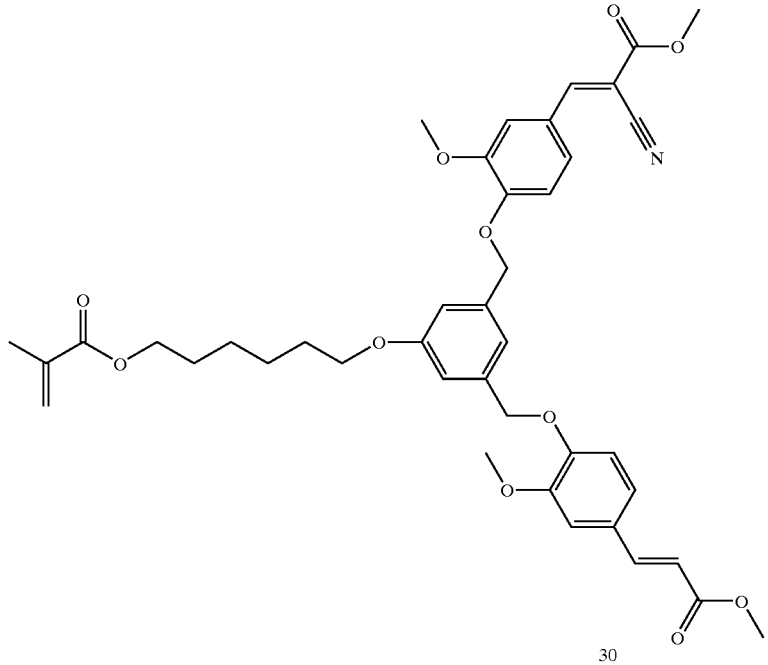

0.32 ml (2 mmol) 1,8-diazabicyclo[5.4.0]undec-7-ene(1, 5-5) (DBU) in 2 ml N,N-dimethylformamide (DMF) were added dropwise to a solution of 0.2 ml (1.9 mmol) 2-methylacrylic acid in 2 ml DMF. After addition of 2 mg phenothiazine, 60 mg tetrabutylammonium iodide and 1.1 g (1.6 mmol) (E)-3-[4-[[3-[(6-chlorohexyl)oxy]-5-[[2-methoxy-4[(E)-2-(methoxycarbonyl)vinyl]phenoxy] methyl]benzyl]oxy]-3-methoxyphenyl]-2-cyanoacrylic acid methyl ester in 7 ml DMF the resulting mixture was stirred at 80° C. for 20 hours. The reaction mixture was poured into an ice cold 1 M HCl solution. The aqueous phase was extracted three times with ethyl acetate. The organic phase was washed with a saturated sodium bicarbonate solution and repeatedly with water, dried over magnesium sulfate, filtered and concentrated by vacuum evaporation. The crude product was filtered through a thin silica gel layer. (eluent: ethyl acetate). The filtrate was evaporated to dryness and recrystallized from ethanol to yield 0.35 g (30%) of 2-methylacrylic acid 6-[3-[2-methoxy-4-[2-cyano-(E)-2-(methoxycarbonyl)vinyl]phenoxymethyl]-5-[2-methoxy-4-[(E)-2-(methoxycarbonyl)vinyl]phenoxymethyl]phenoxy] hexyl ester as slightly yellow crystals.

Example 9

Preparation of Poly-[1-[6-[3,5-bis[[2-methoxy-4-[(E)-2-(methoxycarbonyl)vinyl]phenoxy]methyl] cyclohexyloxy]hexyloxycarbonyl]-1-methyl-ethylene]

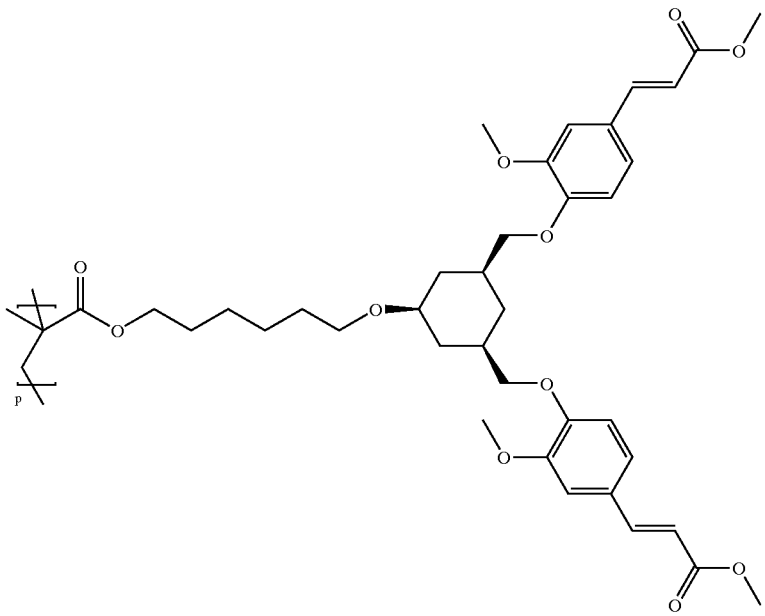

A solution of 0.5 g (0.7 mmol) 2-methylacrylic acid 6[-3,5-bis[[2-methoxy-4-[(E)-2-(methoxycarbonyl)vinyl]phenoxy]methyl]cyclohexyloxy]hexyl ester and 1.1 mg (0.007 mmol) α.α'-azoisobutyronitrile (AIBN) in 1.7 ml dry tetrahydrofuran (THF) was degassed in a Schlenk tube and sealed under argon. The mixture was stirred at 55° C. for 38 h. The resulting polymer was precipitated into 500 ml diethylether and collected. The polymer was reprecipitated from 3.5 ml THF into 500 ml diethylether to yield 0.29 g (58%) Poly-[1-[6-[3,5-bis[[2-methoxy-4-[(E)-2-(methoxycarbonyl)vinyl]phenoxy]methyl]cyclohexyloxy]hexyloxycarbonyl]-1-methyl-ethylene] as a white solid.

The 2-methylacrylic acid 6-[3,5-bis[[2-methoxy-4-[(E)-2-(methoxycarbonyl)vinyl]phenoxy]methyl]cyclohexyloxy]hexyl ester used as stating material was prepared in accordance with the following procedure:

Preparation of 5-[(6-Chlorohexyl)oxy]-1,3-cyclohexanedicarboxylic acid dimethyl ester

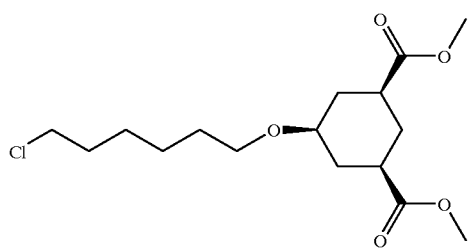

7.5 g (22.8 mmol) 5-[(6-chlorohexyl)oxy]isophthalic acid dimethyl ester (example 6) were dissolved in 75 ml ethyl acetate and charged into a steel autoclave. After addition of 3 g of a hydrogenation catalyst (5% Rh/Alox, Johnson Matthey Company) the vessel was closed and the compound was hydrogenated at a reaction temperature of 70° C. using a constant hydrogen pressure of 18 bar until no further hydrogen uptake was observed (approx. 4 hours). The reaction suspension was cooled to room temperature, filtered and concentrated under vacuum to dryness. The crude product was essentially a cis/trans mixture of 5-[(6-chlorohexyl)oxy]-1,3-cyclohexanedicarboxylic acid dimethyl ester. The pure cis-compound was isolated as a colourless oil by chromatography on silica gel using hexane/ethyl acetate (4:1) as eluent. (yield: 6.1 g, 80%).

Preparation of [3-[(6-Chlorohexyl)oxy]-5-[hydroxymethyl]cyclohexyl]methanol

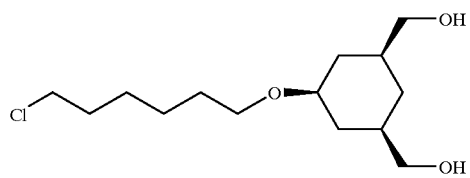

6.05 g (17.5 mmol) cis-5-[(6-chlorohexyl)oxy]-1,3-cyclohexanedicarboxylic acid dimethyl ester were dissolved in 60 ml tetrahydrofuran in an atmosphere of argon. The colourless solution was cooled to −25° C. and then 37 ml (36.9 mmol) of a 1 molar solution of lithiumaluminiumydrid in tetahydrofuran were added dropwise over a period of 45 minutes. The reaction mire was carefully quenched in sequence first with 5 ml of methanol and then with 50 ml of a 1 molar solution of HCl in water. The suspension was stirred for 1 hour at room temperature and subsequently filtered through speedex. The solid residue was washed carefully with 100 ml of tert.-butyl-methylether. The organic phase of the filtrate was separated, washed with 100 ml of a saturated sodium bicarbonate solution and 100 ml of water, dried over magnesium sulfate, filtered and concentrated in vacuum. Column chromatography of the crude product on 280 g of silica gel using dichloromethane:methanol (19:1) as eluent gave 4.6 g (94%) of [3-[(6-chlorohexyl)oxy]-5-[hydroxymethyl]cyclohexyl]methanol as a colourless oil.

Preparation of (E)-3-[4-[[3-[(6-Chlorohexyl)oxy]-5-[[2-methoxy-4-[(E)-2-(methylcarbonyl)vinyl]phenoxy]methyl]cyclohexyl]methoxy]-3-methoxyphenyl]acrylic acid methyl ester

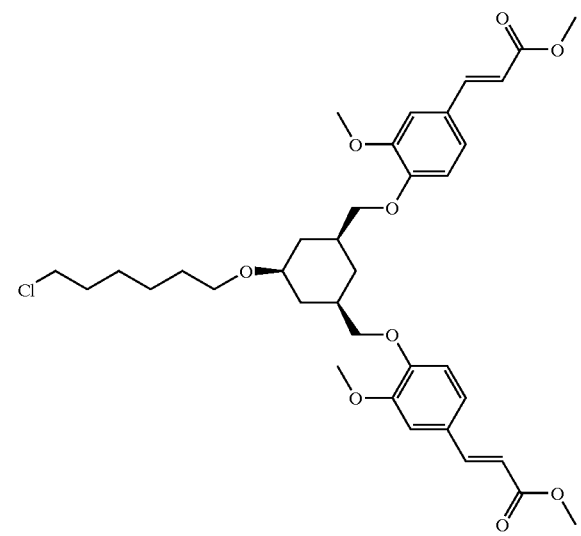

2.25 g (7.9 mmol) [3-[(6-chlorohexyl)oxy]-5-[hydroxymethyl]cyclohexyl]methanol, 4.12 g (19.8 mmol) (E)-4-hydroxy-3-methoxycinnamic acid methyl ester (Example 1) and 5.24 g (19.8 mmol) triphenylphosphine were solved in 25 ml tetrahydrofuran. The solution was cooled to 0° C. and then 8.64 g (19.8 mmol) of a 40% solution of azodicarboxylic acid diethyl ester in toluene were added dropwise over a period of 2 hours. The mixture was allowed to react for 2 hours at 0° C. and then for 24 hours at room temperature. The reaction mixture was concentrated in vacuum. The solid residue was dissolved in 50 ml of dichloromethane, washed with 50 ml of an 1 M HCl solution, 50 ml of a saturated sodium bicarbonate solution and repeatedly with water, dried over magnesium sulfate, filtered and concentrated by vacuum evaporation. The crude product was crystallized from methanol at −20° C. Further purification of the solid residue by chromatography on silica gel using dichloromethane/ethyl acetate (19:1) as eluent gave 2.6 a (50%) of (E)-3-[4-[[3-[(6-chlorohexyl)oxy]-5-[[2-methoxy-4-[(E)-2-(methoxycarbonyl)vinyl]phenoxy]methyl]cyclohexyl]methoxy]-3-methoxyphenyl]acrylic acid methyl ester as a colourless highly viscous oil that solidified on standing.

Preparation of 2-Methylacrylic acid 6-[3,5-bis[[2-methoxy-4-[(E)-2-(methoxycarbonyl)vinyl]phenoxy]methyl]cyclohexyloxy]hexyl ester residue by column chromatography on 270 g silica gel using toluene/ethanol (9:1) as eluent yielded 2.6 g (92%) of 2-methylacrylic acid 6-[3,5-bis[[2-methoxy-4-[(E)-2-

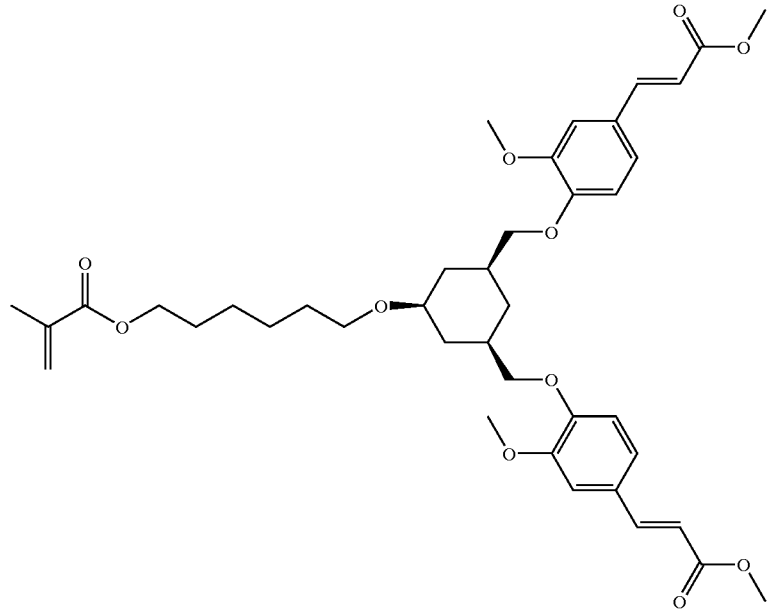

786 mg (5.16 mmol) 1,8-diazabicyclo[5.4.0]undec-7-ene (1,5-5) (DBU) in 5 ml N,N-dimethylformamide were added dropwise to a solution of 413 mg (4.8 mmol) 2-methylacrylic acid in 5 ml N,N-dimethylformamide over a period of 30 minutes. After addition of 4 mg phenothiazine, 146 mg tetrabutylammonium iodide and 2.6 g (3.9 mmol) (E)-3-[4-[[3-[(6-chlorohexyl)oxy]-5-[[2-methoxy-4-[(E)-2-(methoxycarbonyl)vinyl]phenoxy]methyl]cyclohexyl]methoxy]-3-methoxyphenyl]acrylic acid (methoxycarbonyl)vinyl]phenoxy]methyl]cyclohexyloxy]hexyl ester as yellowish oil.

Example 10

A two percent by weight solution S1 of the photoreactive polymer A was prepared using cyclopentanone as a solvent. The solution was stirred for 30 minutes at room temperature.

Photopolymer A:

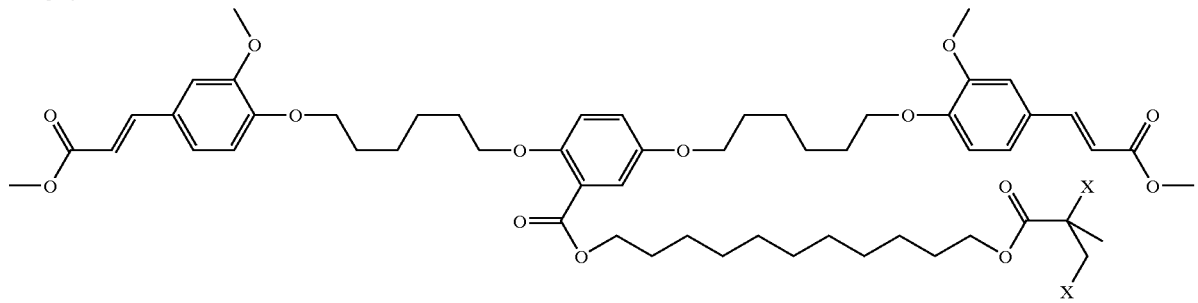

methyl ester dissolved in 10 ml N,N-dimethylformamide the resulting mixture was stirred at 80° C. for 20 hours. The reaction mixture was poured into 50 ml of an ice cold 1 M HCl solution. The aqueous phase was extracted three times with 50 ml ethyl acetate. The organic phase was washed with 50 ml of a saturated sodium bicarbonate solution and repeatedly with water, dried over magnesium sulfate, filtered and concentrated by vacuum evaporation. Purification of the Solution S1 was spin-coated at 2000 rpm onto two ITO (indium-tin-oxide) coated glass plates, which were then dried for 30 minutes at 150° C.

Both substrates were subsequently exposed for one minute to the polarised ultraviolet light of a 200 W high pressure mercury lamp. The intensity of the uv-light at the substrates position was measured as 1.1 mW/cm$^2$.

With the coated sides facing inwards, the two plates were assembled into a parallel liquid crystal cell which was filled with the nematic liquid crystal mixture MLC12000-000 (Merck). Using a polarising microscope, the alignment quality was found to be excellent. With a tilting compensator, which was introduced into the microscope the alignment of the long axis of the liquid crystal molecules was found to be parallel to the polarisation direction of the uv-fight which was used to photo-align photopolymer A.

Example 11

A mixture $M_{LCP}$ was prepared comprising the following liquid crystalline diacrylate monomers:

Mon1:

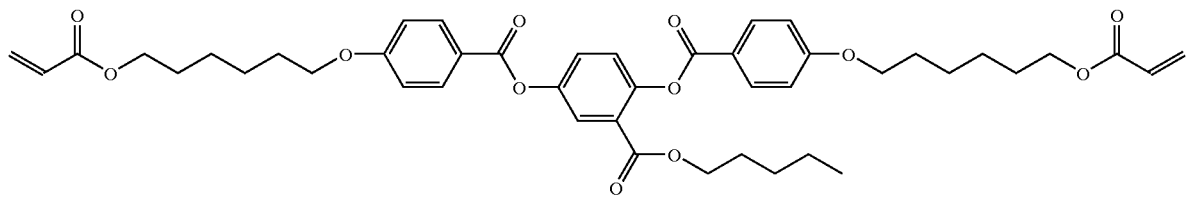

Mon2:

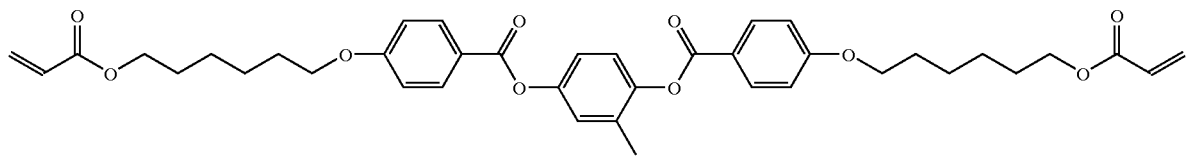

Mon3:

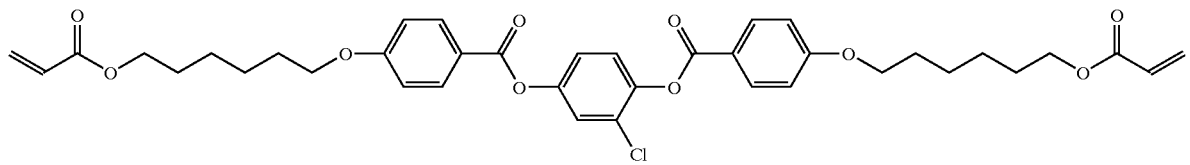

In addition to the diacrylate monomers, photoinitiator IRGACURE 369 from Ciba SC as well as BHT, which served as an inhibitor were added to the mixture. Thus the composition of mixture $M_{LCP}$ was as follows:

| | |
|---|---|
| Mon1 | 77 wt % |
| Mon2 | 14.5 wt % |
| Mon3 | 4.7 wt % |
| Irgacure 369 | 1.9 wt % |
| BHT | 1.9 wt % |

Finally, the solution S(LCP) resulted from dissolving 15 wt % of mixture $M_{LCP}$ in anisole.

Like in example 10, solution S1 was spincoated on a glass plate, dried and subsequently exposed to vertical incident, polarised uv-light for 1 minute. Then diacrylate solution S(LCP) was spin-coated at 800 rpm for 2 minutes on top of the irradiated LPP-layer. To cross-link the liquid crystalline diacrylates the plate was exposed to isotropic uv-light under nitrogen atmosphere for 5 minutes.

To characterise the alignment capability of photopolymer A the contrast of the cross-linked liquid crystal layer was measured using a polarising microscope with crossed polarisers, which was further equipped with a photodiode for light intensity measurements. The contrast was calculated as the ratio of the light intensities measured with the optical axis of the cross-linked liquid crystal layer oriented 45° and 0° in respect to one of the polarisers. The high contrast of 1200:1 demonstrates the excellent alignment capability of photopolymer A.

What is claimed is:

1. A polymeric compound comprising units of formula (I)

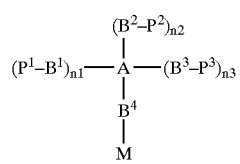

in which:

A represents a nitrogen atom, a carbon atom, a group —CR$^1$— or an aromatic or alicyclic group, which is optionally substituted by a group selected from fluorine, chlorine, cyano and a $C_{1-18}$ cyclic, straight-chain or branched alkyl group, which is optionally substituted by a single cyano group or by one or more halogen atoms and in which one or more non-adjacent alkyl —CH$_2$— groups are optionally replaced by a group selected from —O—, —CO—, —CO—O—, —O—CO—, —Si(CH$_3$)$_2$—O—Si(CH$_3$)$_2$—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C— and —O—CO—O—, wherein R$^1$ represents a hydrogen atom or lower alkyl, M represents a repeating monomer unit;

n$^1$ to n$^3$ each independently represent 0 or an integer having a value of from 1 to 3, with the proviso that 1<n$^1$+n$^2$+n$^3$<4;

P$^1$, P$^2$, P$^3$ each independently represents a photoactive group; and

B$^1$ to B$^4$ each independently represent a residue of general formula II

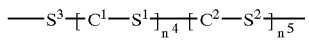

II in which

S$^1$ to S$^3$ each independently represent a single bond or a spacer group selected from a C$_{1-24}$ straight-chain or branched alkylene group, which is optionally substituted by a single cyano group or by one or more halogen atoms and in which one or more non-adjacent alkylene —CH$_2$— groups are optionally replaced by a group selected from —O—, —CO—, —CO—O—, —O—CO—, —Si(CH$_3$)$_2$—O—Si(CH$_3$)$_2$—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C— and —O—CO—O—, wherein R$^1$ is as defined above, C$^1$ and C$^2$ each independently represents an aromatic or an alicyclic group, which is optionally substituted by a group selected from fluorine, chlorine, cyano or a C$_{1-18}$ cyclic, straight-chain or branched alkyl group, which is optionally substituted by a single cyano group or by one or more halogen atoms and in which one or more non-adjacent alkyl —CH$_2$— groups are optionally replaced by a group selected from —O—, —CO—, —CO—O—, —O—CO—, —Si(CH$_3$)$_2$—O—Si(CH$_3$)$_2$—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C— and —O—CO—O—, wherein R$^1$ represents a hydrogen atom or lower alkyl, and n$^4$ and n$^5$ are each independently 0 or 1.

2. A polymeric compound according to claim 1, in which P$^1$ to P$^3$ are selected from the general formulae IIIa and IIIb:

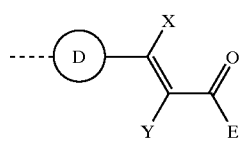

IIIa

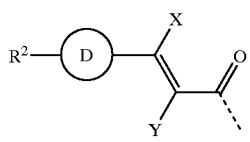

IIIb wherein the broken line indicates the point of linkage to S$^3$ and wherein:

D represents pyrimidine-2,5-diyl, pyridine-2,5diyl, 2,5-thiophenylene, 2,5-furanylene, 1,4- or 2,6-naphthylene; a phenylene group, which is optionally substituted by a group selected from fluorine, chlorine, cyano; or a C$_{1-18}$ cyclic, straight-chain or branched alkyl residue, which is optionally substituted by a single cyano group or by one or more halogen groups and in which one or more non-adjacent alkyl —CH$_2$— groups are optionally replaced by a group selected from —O—, —CO—, —CO—O—, —O—CO—, —Si(CH$_3$)$_2$—O—Si(CH$_3$)$_2$—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C— and —O CO—O—, wherein R$^1$ is as defined above;

E represents —OR$^3$, —NR$^4$R$^5$ or an oxygen atom, which defines together with the ring D a coumarin unit, wherein R$^3$, R$^4$ and R$^5$ are selected from hydrogen and a C$_{1-18}$ cyclic, straight-chain or branched alkyl residue, which is optionally substituted by one or more halogen atoms and in which one or more non-adjacent alkyl —CH$_2$— groups are optionally replaced by a group selected from —O—, —CO—, —CO—O—, —O—CO— and —CH=CH—, or R$^4$ and R$^5$ together form a C$_{5-8}$ alicyclic ring;

X, Y each independently represent hydrogen, fluorine, chlorine, cyano or a C$_{1-12}$ alkyl group, which is optionally substituted by fluorine and in which one or more non-adjacent alkyl —CH$_2$— groups are optionally replaced by a group selected from —O—, —CO—O—, —O—CO— and —CH=CH—;

R$^2$ represents hydrogen or a C$_{1-18}$ straight-chain or branched alkyl residue, which is optionally substituted by a single cyano group or by one or more halogen atoms and in which one or more non-adjacent alkyl —CH$_2$— groups are independently optionally replaced by a group selected from —O—, —CO—, —CO—O—, —O—CO—, —Si(CH$_3$)$_2$—O—Si(CH$_3$)$_2$—, —NR$^1$—, —NR$^1$—CO—, —CO—NR$^1$—, —NR$^1$—CO—O—, —O—CO—NR$^1$—, —NR$^1$—CO—NR$^1$—, —CH=CH—, —C≡C— and —O—CO—O—, wherein R$^1$ is as defined above.

3. A polymeric compound according to claim 1, in which the repeating unit of formula (I) accounts for at least 50% of the monomer building blocks in the compound.

4. A Polymeric compound according to claim 1, in which the group M is selected from acrylate; methacrylate; 2-chloroacrylate; 2-phenylacrylate; acrylamide, methacrylamide, 2-chloroacrylamide and 2-phenylacrylamide, the nitrogen atom of which is optionally substituted by a lower alkyl group; vinyl ether; vinyl ester; a styrene derivative; siloxane; imide; amic acid; an amic acid ester; amidimide; a maleic acid derivative and a fumaric acid derivative.

5. A method of manufacturing a polymeric compound as claimed in claim 1, comprising the polymerization of one or more monomer units of formula (I).

6. A method of manufacturing a polymeric compound as claimed in claim 1 by way of a polymer-analogous reaction, which comprises reacting functional photoactive derivatives with reactive polymers.

7. A polymer layer, comprising a polymeric compound according to claim 1 in cross-linked form.

8. An optical or an electro-optical device, comprising a polymeric compound according to claim 1.

9. An optical or an electro-optical device, comprising a layer according to claim 7.

10. A polymeric compound as claimed in claim 1, which is Poly-[1-[11-[5-[4-[(E)-2-methoxy-carbonylvinyl]benzoyloxy]-2-[6-[2-methoxy-(E)-4-(methoxycarbonyl-vinyl)-phenoxy]oxyhexyl]benzoyloxy]undecyloxy-carbonyl]-1-methylethylene].

11. A polymeric compound as claimed in claim 1, which is Poly-[1-[11-(E,E)-2,5-di-[6-[2-methoxy-4-(methoxycarbonylvinyl)phenoxy]oxyhexyl]benzoyloxy] undecyloxycarbonyl]-1-methylethylene].

* * * * *

UNITED STATES PATENT AND TRADEMARK OFFICE
CERTIFICATE OF CORRECTION

PATENT NO. : 6,833,421 B1
DATED : December 21, 2004
INVENTOR(S) : Guy Marck et al.

It is certified that error appears in the above-identified patent and that said Letters Patent is hereby corrected as shown below:

Title page,
Item [75], Inventors, after "Schlierbach (FR)", insert -- ; Andreas Schuster, Freiburg (DE) --.

Column 51,
Line 64, "pyridine-2,5diyl," should read -- pyridine-2,5-diyl, --.

Column 52,
Line 9, "–O CO–O–," should read -- –O–CO–O–,--.
Line 37, "A Polymeric" should read -- A polymeric --.

Signed and Sealed this

Seventeenth Day of May, 2005

JON W. DUDAS
*Director of the United States Patent and Trademark Office*